US005756476A

United States Patent [19]
Epstein et al.

[11] Patent Number: 5,756,476
[45] Date of Patent: May 26, 1998

[54] INHIBITION OF CELL PROLIFERATION USING ANTISENSE OLIGONUCLEOTIDES

[75] Inventors: Stephen E. Epstein, Rockville, Md.; Edith H. Speir, Annandate, Va.; Ellis F. Unger, Silver Spring, Md.

[73] Assignee: The United States of America as represented by the Department of Health and Human Services, Washington, D.C.

[21] Appl. No.: 187,785

[22] Filed: Jan. 26, 1994

Related U.S. Application Data

[63] Continuation of Ser. No. 821,415, Jan. 14, 1992, abandoned.

[51] Int. Cl.$^6$ .......................... A61K 48/00; C07H 21/00; C12N 5/10; C12Q 1/68
[52] U.S. Cl. .......................... 514/44; 435/375; 435/377; 435/6; 536/24.5
[58] Field of Search .................. 536/22.1, 24.5; 514/44; 435/375, 377, 6

[56] References Cited

U.S. PATENT DOCUMENTS

5,023,243  6/1991  Tullis ................................. 514/44
5,593,974  1/1997  Rosenberg et al. ................. 514/44

OTHER PUBLICATIONS

Simons et al. "Antisense Approach to Smooth Muscle Proliferation", *Supplemental II Circulation* 84(4); (1991).

Ch'ng, et al., "Antisense RNA Complementary to 3' Coding and Noncoding Sequences of Creatine Kinase is a Potent Inhibitor of Translation in Vivo", *Genetics* 86; 10006–10010 (1989).

Dreher, et al., "Expression of Antisense Transcripts Encoding an Extracellular Matrix Protein by Stably Transfected Vascular Smooth Muscle Cells", *European Journal of Cell Biology* 54; 1–9 (1991).

Harel–Bellan, et al., "Specific Inhibition of c–myc Protein Biosynthesis Using an Antisense Synthetic Deoxy–Oligonucleotide in Human T Lymphocytes", *Journal of Immunology* 140 (7); 2431–2435 (1988).

Shoemaker, et al., Use of DNA Sequence and Mutant Analyses and Antisense Oligodeoixynucleotides to Examiner the Molecular Basis of Nonmuscle Myosin Light Chain Kinase Autoinhibition, Calmodulin Recognition, and Activity, *Journal of Cell Biology* 111; 1107–1125 (1990).

Simons, "Naturally Occurring Antisense RNA Control—A Brief Review", *Gene* 72; 35–44 (1988).

Wickstrom, et al., "Human Promyelocytic Leukemia JL–60 Cell Proliferation and c–MYC Protein Expression are Inhibited by an Antisense Pentadecadeoxynucleotide Targeted Against c–MYC mRNA", Proc. Natl. Acad. Sci. USA, 1988, 85:1028–1032.

Holt, et al., "An Oligomer Complementary to c–MYC mRNA Inhibits Proliferation of HL–60 Promyelocytic Cells and Induces Differentiation", Mol. Cell Biol., 1988, 8:963–973.

Heikkila, et al., "A c–MYC Antisense Oligodeoxynucleotide Inhibits Entry into S Phase but not Progress from $G_0$ to $G_1$", Nature, 1987, 328:445–449.

Bacon, et al., "Walking Along Human c–MYC mRNA with Antisense Oligodeoxynucleotides: Maximum Efficacy at the 5' Cap Region", Oncogene Res., 1991, 6:13–19.

Lee et al., Circulation Res., vol. 73 No. 5, pp. 797–807 (Nov. 1993).

Biro et al., PNAS USA, vol. 90, pp. 654–658 (Jan. 1993).

Ledley, Human Gene Therapy, vol. 2 (1991) pp. 77–83.

Santoian et al., Circulation, Supp. I, vol. 86 No. 4 (Oct. 1992), No. 3187.

Morishita et al., PNAS USA, vol. 90, pp. 8474–8478, (Sep. 1993).

Ebbecke et al., Eur. Soc. Cardiol. XIIIth Congress (Aug. 1991) No. 177.

Chapman et al., Circulation Res., vol. 71 No. 1, pp. 27–33 (Jul. 1992).

Takeshita, Circulation, Supp. I, vol. 86 No. 4 (Oct. 1992), No. 0903.

King, R.C. and Stanfield, W.D. "A Dictionary of Genetics" 1990, Oxford University Press.

Jaskulski et al. "Inhibition of Cellular Proliferation by Antisense Oligodeoxynucleotides to PCNA Cyclin." Science 240: 1544–1546, 1988.

Ross, R. "The Pathogenesis of Atherosclerosis—An Update" The New England Journal of Medicine 314: 488–500, 1986.

Uhlmann, E. et al. "Antisense Oligonucleotides: A New Therapeutic Principle" Chemical Reviews 90: 543–584, 1990.

Reilly, C. et al. "Heparin Prevents Vascular Smooth Muscle Cell Progression Through the $G_1$ Phase of the Cell Cycle" J. Biol. Chem. 264: 6990–6995, 1989.

Pines, J. et al. "Isolation of a Human Cyclin cDNA: Evidence for Cyclin mRNA and Protein Regulation in the Cell Cycle and for Interaction with p34$^{cdc2}$" Cell 58:833–846 '89.

Tachibana, K. et al. "The Starfish Egg mRNA Responsible for Meiosis Reinitiation Encodes Cyclin" Devel. Biol. 140 241–252 '90.

*Primary Examiner*—Charles C. P. Rories
*Attorney, Agent, or Firm*—Townsend and Townsend and Crew LLP

[57] ABSTRACT

The present invention provides a method of inhibiting restenosis of a blood vessel in a mammal after mechanical treatment of the vessel to reduce a stenosis. The method includes contacting proliferating smooth muscle cells in the vessel with an antisense oligonucleotide directed against a cellular division cycle gene product. This gene product can be one of the following: c-myc, PCNA, and cyclin $B_1$. The antisense oligonucleotide is used in an amount effective to inhibit translation of the cellular division cycle gene product in the cell.

19 Claims, 3 Drawing Sheets

1 2 3 4

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 8082 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Human ( v i i ) IMMEDIATE SOURCE:
        ( B ) CLONE: C-Myc Genomic Clone ( x i ) SEQUENCE DESCRIPTION: SEQ ID NO:1:

```
AGCTTGTTTG GCCGTTTTAG GGTTTGTTGG AATTTTTTTT TCGTCTATGT ACTTGTGAAT      60
TATTTCACGT TTGCCATTAC CGGTTCTCCA TAGGGTGATG TTCATTAGCA GTGGTGATAG     120
GTTAATTTTC ACCATCTCTT ATGCGGTTGA ATAGTCACCT CTGAACCACT TTTTCCTCCA    180
GTAACTCCTC TTTCTTCGGA CCTTCTGCAG CCAACCTGAA AGAATAACAA GGAGGTGGCT    240
GGAAACTTGT TTAAGGAAC  CGCCTGTCCT TCCCCGCTG  GAAACCTTGC ACCTCGGACG    300
CTCCTGCTCC TGCCCCACC  TGACCCCGC  CCTCGTTGAC ATCCAGGCGC GATGATCTCT    360
GCTGCCAGTA GAGGGCACAC TTACTTTACT TTCGCAAACC TGAACGCGGG TGCTGCCCAG    420
AGAGGGGGCG GAGGGAAAGA CGCTTTGCAG CAAAATCCAG CATAGCGATT GGTTGCTCCC    480
CGCGTTTGCG GCAAAGGCCT GGAGGCAGGA GTAATTTGCA ATCCTTAAAG CTGAATTGTG    540
CAGTGCATCG GATTTGGAAG CTACTATATT CACTTAACAC TTGAACGCTG AGCTGCAAAC    600
TCAACGGGTA ATAACCCATC TTGAACAGCG TACATGCTAT ACACACACCC CTTTCCCCCG    660
AATTGTTTC  TCTTTTGGAG GTGGTGGAGG GAGAGAAAAG TTTACTTAAA ATGCCTTTGG    720
GTGAGGGACC AAGGATGAGA AGAATGTTTT TTGTTTTTCA TGCCGTGGAA TAACACAAAA    780
TAAAAAATCC CGAGGGAATA TACATTATAT ATTAAATATA GATCATTTCA GGGAGCAAAC    840
AAATCATGTG TGGGGCTGGG CAACTAGCTG AGTCGAAGCG TAAATAAAAT GTGAATACAC    900
GTTTGCGGGT TACATACAGT GCACTTTCAC TAGTATTCAG AAAAAATTGT GAGTCAGTGA    960
ACTAGGAAAT TAATGCCTGG AAGGCAGCCA AATTTTAATT AGCTCAAGAC TCCCCCCCCC   1020
CCCCAAAAAA AGGCACGGAA GTAATACTCC TCTCCTCTTC TTTGATCAGA ATCGATGCAT   1080
TTTTTGTGCA TGACCGCATT TCCAATAATA AAGGGGAAA  GAGGACCTGG AAAGGAATTA   1140
AACGTCCGGT TTGTCCGGGG AGGAAAGAGT TAACGGTTTT TTTCACAAGG GTCTCTGCTG   1200
ACTCCCCCGG CTCGGTCCAC AAGCTCTCCA CTTGCCCCTT TTAGGAAGTC CGGTCCCGCG   1260
GTTCGGGTAC CCCCTGCCCC TCCATATTC  TCCCGTCTAG CACCTTTGAT TTCTCCCAAA   1320
CCCGGCAGCC CGAGACTGTT GCAAACCGGC GCCACAGGGC GCAAGGGGA  TTTGTCTCTT   1380
CTGAAACCTG GCTGAGAAAT TGGGAACTCC GTGTGGGAGG CGTGGGGTG  GGACGGTGGG   1440
GTACAGACTG GCAGAGAGCA GGCAACCTCC CTCTCGCCCT AGCCCAGCTC TGGAACAGGC   1500
```

```
AGACACATCT CAGGGCTAAA CAGACGCCTC CCGCACGGGG CCCCACGGAA GCCTGAGCAG  1560
GCGGGGCAGG AGGGGCGGTA TCTGCTGCTT TGGCAGCAAA TTGGGGGACT CAGTCTGGGT  1620
GGAAGGTATC CAATCCAGAT AGCTGTGCAT ACATAATGCA TAATACATGA CTCCCCCCAA  1680
CAAATGCAAT GGGAGTTTAT TCATAACGCG CTCTCCAAGT ATACGTGGCA ATGCGTTGCT  1740
GGGTTATTTT AATCATTCTA GGCATCGTTT TCCTCCTTAT GCCTCTATCA TTCCTCCCTA  1800
TCTACACTAA CATCCCACGC TCTGAACGCG CGCCCATTAA TACCCTTCTT TCCTCCACTC  1860
TCCCTGGGAC TCTTGATCAA AGCGCGGCCC TTTCCCAGC  CTTAGCGAGG CGCCCTGCAG  1920
CCTGGTACGC GCGTGGCGTG GCGGTGGGCG CGCAGTGCGT TCTCTGTGTG GAGGGCAGCT  1980
GTTCCGCCTG CGATGATTTA TACTCACAGG ACAAGGATGC GGTTTGTCAA ACAGTACTGC  2040
TACGGAGGAG CAGCAGAGAA AGGGAGAGGG TTTGAGAGGG AGCAAAAGAA AATGGTAGGC  2100
GCGCGTAGTT AATTCATGCG GCTCTCTTAC TCTGTTTACA TCCTAGAGCT AGAGTGCTCG  2160
GCTGCCCGGC TGAGTCTCCT CCCCACCTTC CCCACCCTCC CCACCCTCCC CATAAGCGCC  2220
CCTCCCGGGT TCCCAAAGCA GAGGGCGTGG GGGAAAAGAA AAAAGATCCT CTCTCGCTAA  2280
TCTCCGCCCA CCGGCCCTTT ATAATGCGAG GGTCTGGACG GCTGAGGACC CCCGAGCTGT  2340
GCTGCTCGCG GCCGCCACCG CCGGGCCCCG GCCGTCCCTG GCTCCCTCC  TGCCTCGAGA  2400
AGGGCAGGGC TTCTCAGAGG CTTGGCGGGA AAAGAACGG  AGGGAGGGAT CGCGCTGAGT  2460
ATAAAGCCG  GTTTCGGGG  CTTTATCTAA CTCGCTGTAG TAATTCCAGC GAGAGGCAGA  2520
GGGAGCGAGC GGGCGGCCGG CTAGGGTGGA AGAGCCGGGC GAGCAGAGCT GCGCTGCGGG  2580
CGTCCTGGGA AGGGAGATCC GGAGCGAATA GGGGCTTCG  CCTCTGGCCC AGCCCTCCCG  2640
CTGATCCCCC AGCCAGCGGT CCGCAACCCT TGCCGCATCC ACGAAACTTT GCCCATAGCA  2700
GCGGGCGGGC ACTTTGCACT GGAACTTACA ACACCCGAGC AAGGACGCGA CTCTCCCGAC  2760
GCGGGGAGGC TATTCTGCCC ATTTGGGGAC ACTTCCCCGC CGCTGCCAGG ACCCGCTTCT  2820
CTGAAAGGCT CTCCTTGCAG CTGCTTAGAC GCTGGATTTT TTCGGGTAG  TGGAAAACCA  2880
GGTAAGCACC GAAGTCCACT TGCCTTTTAA TTTATTTTTT TATCACTTTA ATGCTGAGAT  2940
GAGTCGAATG CCTAAATAGG GTGTCTTTTC TCCCATTCCT GCGCTATTGA CACTTTTCTC  3000
AGAGTAGTTA TGGTAACTGG GGCTGGGGTG GGGGGTAATC CAGAACTGGA TCGGGGTAAA  3060
GTGACTTGTC AAGATGGGAG AGGAGAAGGC AGAGGGAAAA CGGGAATGGT TTTTAAGACT  3120
ACCCTTTCGA GATTTCTGCC TTATGAATAT ATTCACGCTG ACTCCCGGCC GGTCGGACAT  3180
TCCTGCTTTA TTGTGTTAAT TGCTCTCTGG GTTTGGGGG  GCTGGGGGTT GCTTTGCGGT  3240
GGGCAGAAAG CCCCTTGCAT CCTGAGCTCC TTGGAGTAGG GACCGCATAT CGCCTGTGTG  3300
AGCCAGATCG CTCCGCAGCC GCTGACTTGT CCCCGTCTCC GGGAGGGCAT TTAAATTTCG  3360
GCTCACCGCA TTTCTGACAG CCGGAGACGG ACACTGCGGC GCGTCCCGCC CGCCTGTCCC  3420
CGCGGCGATT CCAACCCGCC CTGATCCTTT TAAGAAGTTG GCATTTGGCT TTTTAAAAAG  3480
CAATAATACA ATTTAAAACC TGGGTCTCTA GAGGTGTTAG GACGTGGTGT TGGGTAGGCG  3540
CAGGCAGGGG AAAAGGGAGG CGAGGATGTG TCCGATTCTC CTGGAATCGT TGACTTGGAA  3600
AAACCAGGGC GAATCTCCGC ACCCAGCCCT GACTCCCCTG CCGCGGCCGC CCTCGGGTGT  3660
CCTCGCGCCC GAGATGCGGA GGAACTGCGA GGAGCGGGGC TCTGGGCGGT TCCAGAACAG  3720
CTGCTACCCT TGGTGGGGTG GCTCCGGGGG AGGTATCGCA GCGGGGTCTC TGGCGCAGTT  3780
GCATCTCCGT ATTGAGTGCG AAGGGAGGTG CCCCTATTAT TATTTGACAC CCCCCTTGTA  3840
TTTATGGAGG GGTGTTAAAG CCCGCGGCTG AGCTCGCCAC TCCAGCCGGC GAGAGAAAGA  3900
```

```
AGAAAAGCTG GCAAAAGGAG TGTTGGACGG GGGCGGTACT GGGGGTGGGG ACGGGGCGG   3960
TGGAGAGGGA AGGTTGGGAG GGGCTGCGGT GCCGGCGGGG GTAGGAGAGC GGCTAGGGCG  4020
CGAGTGGGAA CAGCCGCAGC GGAGGGGCCC CGGCGCGGAG CGGGGTTCAC GCAGCCGCTA  4080
GCGCCCAGGC GCCTCTCGCC TTCTCCTTCA GGTGGCGCAA AACTTTGTGC CTTGGATTTT  4140
GGCAAATTGT TTTCCTCACC GCCACCTCCC GCGGCTTCTT AAGGGCGCCA GGGCCGATTT  4200
CGATTCCTCT GCCGCTGCGG GGCCGACTCC CGGGCTTTGC GCTCCGGGCT CCCGGGGGAG  4260
CGGGGGCTCG GCGGGCACCA AGCCGCTGGT TCACTAAGTG CGTCTCCGAG ATAGCAGGGG  4320
ACTGTCCAAA GGGGGTGAAA GGGTGCTCCC TTTATTCCCC CACCAAGACC ACCCAGCCGC  4380
TTTAGGGGAT AGCTCTGCAA GGGGAGAGGT TCGGGACTGT GGCGCGCACT GCGCGCTGCG  4440
CCAGGTTTCC GCACCAAGAC CCCTTTAACT CAAGACTGCC TCCCGCTTTG TGTGCCCCGC  4500
TCCAGCAGCC TCCCGCGACG ATGCCCCTCA ACGTTAGCTT CACCAACAGG AACTATGACC  4560
TCGACTACGA CTCGGTGCAG CCGTATTTCT ACTGCGACGA GGAGGAGAAC TTCTACCAGC  4620
AGCAGCAGCA GAGCGAGCTG CAGCCCCCGG CGCCCAGCGA GGATATCTGG AAGAAATTCG  4680
AGCTGCTGCC CACCCCGCCC CTGTCCCCTA GCCGCCGCTC CGGGCTCTGC TCGCCCTCCT  4740
ACGTTGCGGT CACACCCTTC TCCCTTCGGG GAGACAACGA CGGCGGTGGC GGGAGCTTCT  4800
CCACGGCCGA CCAGCTGGAG ATGGTGACCG AGCTGCTGGG AGGAGACATG GTGAACCAGA  4860
GTTTCATCTG CGACCCGGAC GACGAGACCT TCATCAAAAA CATCATCATC CAGGACTGTA  4920
TGTGGAGCGG CTTCTCGGCC GCCGCCAAGC TCGTCTCAGA GAAGCTGGCC TCCTACCAGG  4980
CTGCGCGCAA AGACAGCGGC AGCCCGAACC CGCCCGCGG CCACAGCGTC TGCTCCACCT  5040
CCAGCTTGTA CCTGCAGGAT CTGAGCGCCG CCGCCTCAGA GTGCATCGAC CCCTCGGTGG  5100
TCTTCCCCTA CCCTCTCAAC GACAGCAGCT CGCCCAAGTC CTGCGCCTCG CAAGACTCCA  5160
GCGCCTTCTC TCCGTCCTCG GATTCTCTGC TCTCCTCGAC GGAGTCCTCC CCGCAGGGCA  5220
GCCCCGAGCC CCTGGTGCTC CATGAGGAGA CACCGCCCAC CACCAGCAGC GACTCTGGTA  5280
AGCGAAGCCC GCCCAGGCCT GTCAAAAGTG GGCGGCTGGA TACCTTTCCC ATTTTCATTG  5340
GCAGCTTATT TAACGGGCCA CTCTTATTAG GAAGGAGAGA TAGCAGATCT GGAGAGATTT  5400
GGGAGCTCAT CACCTCTGAA ACCTTGGGCT TTAGCGTTTC CTCCCATCCC TTCCCCTTAG  5460
ACTGCCCATG TTTGCAGCCC CCCTCCCCGT TTGTCTCCCA CCCCTCAGGA ATTTCATTTA  5520
GGTTTTTAAA CCTTCTGGCT TATCTTACAA CTCAATCCAC TTCTTCTTAC CTCCCGTTAA  5580
CATTTAATT GCCCTGGGGC GGGGTGGCAG GGAGTGTATG AATGAGGATA AGAGAGGATT  5640
GATCTCTGAG AGTGAATGAA TTGCTTCCCT CTTAACTTCC GAGAAGTGGT GGGATTTAAT  5700
GAACTATCTA CAAAAATGAG GGCTGTGTT TAGAGGCTAG GCAGGGCCTG CCTGAGTGCG  5760
GGAGCCAGTG AACTGCCTCA AGAGTGGGTG GGCTGAGGAG CTGGGATCTT CTCAGCCTAT  5820
TTTGAACACT GAAAAGCAAA TCCTTGCCAA AGTTGGACTT TTTTTTTTCT TTATTCCTT   5880
CCCCCGCCCT CTTGGACTTT TGGCAAAACT GCAATTTTT TTTTTTATT TTTCATTTCC   5940
AGTAAAATAG GGAGTTGCTA AAGTCATACC AAGCAATTTG CAGCTATCAT TTGCAACACC  6000
TGAAGTGTTC TTGGTAAAGT CCCTCAAAAA TAGGAGGTGC TTGGGAATGT GCTTTGCTTT  6060
GGGTGTGTCC AAAGCCTCAT TAAGTCTTAG GTAAGAATTG GCATCAATGT CCTATCCTGG  6120
GAAGTTGCAC TTTTCTTGTC CATGCCATAA CCCAGCTGTC TTTCCCTTTA TGAGACTCTT  6180
ACCTTCATGG TGAGAGGAGT AAGGGTGGCT GGCTAGATTG GTTCTTTTTT TTTTTTTTC   6240
CTTTTTTAAG ACGGAGTCTC ACTCTGTCAC TAGGCTGGAG TGCAGTGGCG CAATCAACCT  6300
```

-continued

```
CCAACCCCCT GGTTCAAGAG ATTCTCCTGC CTCAGCCTCC CAAGTAGCTG GGACTACAGG    6360
TGCACACCAC CATGCCAGGC TAATTTTTGT AATTTTAGTA GAGATGGGGT TTCATCGTGT    6420
TGGCCAGGAT GGTCTCTCCT GACCTCACGA TCCGCCCACC TCGGCCTCCC AAAGTGCTGG    6480
GATTACAGGT GTGAGCCAGG GCACCAGGCT TAGATGTGGC TCTTTGGGGA GATAATTTTG    6540
TCCAGAGACC TTTCTAACGT ATTCATGCCT TGTATTTGTA CAGCATTAAT CTGGTAATTG    6600
ATTATTTTAA TGTAACCTTG CTAAAGGAGT GATTTCTATT TCCTTCTTA  AAGAGGAGGA    6660
ACAAGAAGAT GAGGAAGAAA TCGATGTTGT TTCTGTGGAA AAGAGGCAGG CTCCTGGCAA    6720
AAGGTCAGAG TCTGGATCAC CTTCTGCTGG AGGCCACAGC AAACCTCCTC ACAGCCCACT    6780
GGTCCTCAAG AGGTGCCACG TCTCCACACA TCAGCACAAC TACGCAGCGC CTCCCTCCAC    6840
TCGGAAGGAC TATCCTGCTG CCAAGAGGGT CAAGTTGGAC AGTGTCAGAG TCCTGAGACA    6900
GATCAGCAAC AACCGAAAAT GCACCAGCCC CAGGTCCTCG GACACCGAGG AGAATGTCAA    6960
GAGGCGAACA CACAACGTCT TGGAGCGCCA GAGGAGGAAC GAGCTAAAAC GGAGCTTTTT    7020
TGCCCTGCGT GACCAGATCC CGGAGTTGGA AAACAATGAA AAGGCCCCA  AGGTAGTTAT    7080
CCTTAAAAAA GCCACAGCAT ACATCCTGTC CGTCCAAGCA GAGGAGCAAA AGCTCATTTC    7140
TGAAGAGGAC TTGTTGCGGA AACGACGAGA ACAGTTGAAA CACAAACTTG AACAGCTACG    7200
GAACTCTTGT GCGTAAGGAA AAGTAAGGAA AACGATTCCT TCTAACAGAA ATGTCCTGAG    7260
CAATCACCTA TGAACTTGTT TCAAATGCAT GATCAAATGC AACCTACAA  CCTTGGCTGA    7320
GTCTTGAGAC TGAAAGATTT AGCCATAATG TAAACTGCCT CAAATTGGAC TTTGGGCATA    7380
AAAGAACTTT TTTATGCTTA CCATCTTTTT TTTTTCTTTA ACAGATTTGT ATTAAGAAT    7440
TGTTTTTAAA AAATTTTAAG ATTTACACAA TGTTTCTCTG TAAATATTGC CATTAAATGT    7500
AAATAACTTT AATAAAACGT TTATAGCAGT TACACAGAAT TTCAATCCTA GTATATAGTA    7560
CCTAGTATTA TAGGTACTAT AAACCCTAAT TTTTTTATT  TAAGTACATT TTGCTTTTA    7620
AAGTTGATTT TTTTCTATTG TTTTAGAAA  AAATAAAATA ACTGGCAAAT ATATCATTGA    7680
GCCAAATCTT AAGTTGTGAA TGTTTTGTTT CGTTTCTTCC CCCTCCCAAC CACCACCATC    7740
CCTGTTTGTT TTCATCAATT GCCCCTTCAG AGGGCGGTCT TAAGAAGGC  AAGAGTTTTC    7800
CTCTGTTGAA ATGGGTCTGG GGGCCTTAAG GTCTTTAAGT TCTTGGAGGT TCTAAGATGC    7860
TTCCTGGAGA CTATGATAAC AGCCAGAGTT GACAGTTAGA AGGAATGGCA GAAGGCAGGT    7920
GAGAAGGTGA GAGGTAGGCA AGGAGATAC  AAGAGGTCAA AGGTAGCAGT TAAGTACACA    7980
AAGAGGCATA AGGACTGGGG AGTTGGGAGG AAGGTGAGGA AGAAACTCCT GTTACTTTAG    8040
TTAACCAGTG CCAGTCCCCT GCTCACTCCA AACCCAGGAA TT                      8082
```

( 2 ) INFORMATION FOR SEQ ID NO:2:

( i ) SEQUENCE CHARACTERISTICS:
        ( A ) LENGTH: 1452 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Human ( v i i ) IMMEDIATE SOURCE:
        ( B ) CLONE: Cyclin B1 cDNA clone ( x i ) SEQUENCE DESCRIPTION: SEQ ID NO:2:

| | | | | | |
|---|---|---|---|---|---|
| TTGGTTTCTG | CTGGGTGTAG | GTCCTTGGCT | GGTCGGGCTC | CGGTGTTCTG | CTTCTCCCCG | 60
| CTGAGCTGCT | GCCTGGTGAA | GAGGAAGCCA | TGGCGCTCCG | AGTCACCAGG | AACTCGAAAA | 120
| TTAATGCTGA | AAATAAGGCG | AAGATCAACA | TGGCAGGCGC | AAAGCGCGTT | CCTACGGCCC | 180
| CTGCTGCAAC | CTCCAAGCCC | GGACTGAGGC | CAAGAACAGC | TCTTGGGGAC | ATTGGTAACA | 240
| AAGTCAGTGA | ACAACTGCAG | GCCAAAATGC | CTATGAAGAA | GGAAGCAAAA | CCTTCAGCTA | 300
| CTGGAAAAGT | CATTGATAAA | AAACTACCAA | AACCTCTTGA | AAAGGTACCT | ATGCTGGTGC | 360
| CAGTGCCAGT | GTCTGAGCCA | GTGCCAGAGC | CAGAACCTGA | GCCAGAACCT | GAGCCTGTTA | 420
| AAGAAGAAAA | ACTTTCGCCT | GAGCCTATTT | TGGTTGATAC | TGCCTCTCCA | AGCCCAATGG | 480
| AAACATCTGG | ATGTGCCCCT | GCAGAAGAAG | ACCTGTGTCA | GGCTTTCTCT | GATGTAATTC | 540
| TTGCAGTAAA | TGATGTGGAT | GCAGAAGATG | GAGCTGATCC | AAACCTTTGT | AGTGAATATG | 600
| TGAAAGATAT | TTATGCTTAT | CTGAGACAAC | TTGAGGAAGA | GCAAGCAGTC | AGACCAAAAT | 660
| ACCTACTGGG | TCGGGAAGTC | ACTGGAAACA | TGAGAGCCAT | CCTAATTGAC | TGGCTAGTAC | 720
| AGGTTCAAAT | GAAATTCAGG | TTGTTGCAGG | AGACCATGTA | CATGACTGTC | TCCATTATTG | 780
| ATCGGTTCAT | GCAGAATAAT | TGTGTGCCCA | AGAAGATGCT | GCAGCTGGTT | GGTGTCACTG | 840
| CCATGTTTAT | TGCAAGCAAA | TATGAAGAAA | TGTACCCTCC | AGAAATTGGT | GACTTTGCTT | 900
| TTGTGACTGA | CAACACTTAT | ACTAAGCACC | AAATCAGACA | GATGGAAATG | AAGATTCTAA | 960
| GAGCTTTAAA | CTTTGGTCTG | GGTCGGCCTC | TACCTTTGCA | CTTCCTTCGG | AGAGCATCTA | 1020
| AGATTGGAGA | GGTTGATGTC | GAGCAACATA | CTTTGGCCAA | ATACCTGATG | GAACTAACTA | 1080
| TGTTGGACTA | TGACATGGTG | CACTTTCCTC | CTTCTCAAAT | TGCAGCAGGA | GCTTTTTGCT | 1140
| TAGCACTGAA | AATTCTGGAT | AATGGTGAAT | GGACACCAAC | TCTACAACAT | TACCTGTCAT | 1200
| ATACTGAAGA | ATCTCTTCTT | CCAGTTATGC | AGCACCTGGC | TAAGAATGTA | GTCATGGTAA | 1260
| ATCAAGGACT | TACAAAGCAC | ATGACTGTCA | AGAACAAGTA | TGCCACATCG | AAGCATGCTA | 1320
| AGATCAGCAC | TCTACCACAG | CTGAATTCTG | CACTAGTTCA | AGATTTAGCC | AAGGCTGTGG | 1380
| CAAAGGTGTA | ACTTGTAAAC | TTGAGTTGGA | GTACTATACT | TTACAAACTA | AAATTGGCAC | 1440
| ATGTGCATCT | GT | | | | | 1452

( 2 ) INFORMATION FOR SEQ ID NO:3:

( i ) SEQUENCE CHARACTERISTICS:
        ( A ) LENGTH: 6340 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Human ( v i i ) IMMEDIATE SOURCE:
        ( B ) CLONE: PCNA Genomic Clone ( x i ) SEQUENCE DESCRIPTION: SEQ ID NO:3:

| | | | | | |
|---|---|---|---|---|---|
| GAATTCTGCT | GACCAAGGTA | TTAAAAGTAA | CTAAAGAGAA | GTGGTGTGAA | GAAAGCAAGA | 60
| GAGAAACAAC | AAATCCTGTC | CATCCTGTAA | CAATTGAAAA | TTTCTGGCTG | GGCGTGGTGG | 120

```
CTCAGGCCTG  TAATCCCAGC  ACTTTGAGAG  GCCGAGGCAG  GTGGATCACC  TGAGGTCAGG    180

TGTTCAAGAC  CAGCCTGGCC  AACATGGTGA  AACCCCGTCT  CTACTAAAAA  AAAATAATAA    240

TAATAATACA  AAAATTAGCC  GGGTGTGGTG  GTAGGCACCT  GTAATCCCAG  ATACTCGGGA    300

GGCTGAGGCA  GGAGACTCAC  TTGAACCTGG  GAGGCGGAGG  TTGCAATGAG  CTGAGATCGC    360

GCGACTGTAC  TCCAGCCTGG  ATGACAGAGC  AGGACTCCAT  CTCAAAAAGG  AAGGCGGGGA    420

AAAGGGGAAA  TATTAAATGT  GTACGCTCTT  TGACTCAGCT  GTATTACTTC  AAGGAGTTGA    480

TATCACCAAA  ATTGCCTAAG  TGCTCAAAGG  TGTTTGTAGT  TAAACAACAG  GAGATTGATA    540

AATTATGTTA  TATACATGTG  ATGCTATGTT  TTAAAGAGGT  ACTGATATGA  TAAAAAGATG    600

TACGTGGCAT  AAAATTAAAT  GTACTTATTA  AGTACTTTTC  CAAGTGTTTA  CGGAATGAGT    660

GCATTTTTGA  AAAAAAAAAA  GTGTATTCGA  ACTTTAAAA   AAGCTTTAAA  AGCTTTATAC    720

AATAACGATT  GAGTGATTAT  AAGAGCTGGC  GGGGGAATGT  TAAGAGGATG  ATAGGGAGCT    780

AAGTTTAACA  GAACAATTCA  CCTCTTTATC  TTGTGACACC  TACGAGCGCA  TCAATTCTGT    840

AATTGAAAAA  TAAAGTGCAT  ATTTGCAGCA  GCTGTACTCT  CTTCAGGCTG  CAAGGAGGCT    900

TTTCCTCCCG  GTAGGCTTGA  TTTGCATTTC  ACTTTCACTT  TCGTGGCTGG  AAACTTTCTA    960

CCCACGTAGT  GAGGCTAGAG  GAGCCACCTA  AGCTGGGGC   TTGACGAAGC  CGGGACCGGG   1020

ACCCGATCTC  CACATATGCC  CGGACTTCTT  CTGCGGCCGG  GTTCAGGAGT  CAAAGAGGCG   1080

GGGAGACCTG  CGCGACGCTG  CCCCGCCCTG  CGCCGCTTC   CTCCAATGTA  TGCTCTAGGG   1140

GGCGGGCCTC  GCGGGGAGCA  TGGACACGAT  TGGCCCTAAA  GTCTTCCCCG  CAAGGCCGTG   1200

GGCTGGACAG  CGTGGTGACG  TCGCAACGCG  GCGCAGGGTG  AGAGCGCGCG  CTTGCGGACG   1260

CGGCGGCATT  AAACGGTTGC  AGGCGTAGAG  AGTGGTCGTT  GTCTTTCTAG  GTCTCAGCCG   1320

GTCGTCGCGA  CGTTCGCCCG  CTCGCTCTGA  GGCTCCTGAA  GCCGAAACTA  GCTAGACTTT   1380

CCTCCTTCCC  GCCTGCCTGT  AGCGGCGTTG  TTGCCACTCC  GCCACCATGT  TCGAGGCGCG   1440

CCTGGTCCAG  GGCTCCATCC  TCAAGAAGGT  GTTGGAGGCA  CTCAAGGACC  TCATCAACGA   1500

GGCCTGCTGG  GATATTAGCT  CCAGCGGTGT  AAACCTGCAG  AGCATGGACT  CGTCCACGT    1560

CTCTTTGGTG  CAGCTCACCC  TGCGGTCTGA  GGGCTTCGAC  ACCTACCGCT  GCGACCGCAA   1620

CCTGGCCATG  GGCGTGAACC  TCACCAGGTG  AGCCTCGCGC  CCCGGGAAGC  CGCCCCGGCC   1680

CGCCTGCACC  TCCGGCTGTG  GCGAGCGCTT  CGAGCCTAGC  CCTCATTGGC  TGGCGTGGGC   1740

ATCCAGAGCT  TCTCATTGGC  CTGCACGCAG  TGGTGGGGCC  CAAGCTGAGA  TGAGCGGTTA   1800

CGGAAAAGCC  CGCGCTGGCT  GCTGCGCGAA  CCTGCTTTTT  CGCGCCAAAG  TCACAAAGCG   1860

GGTGGTGGCG  GGAAAATCAA  GGGTTTTTCC  GCAGTGCCAG  GAACACTGTT  CCAGGGACTC   1920

TTTGCTCACT  AAACCTGTTG  GCCTTGAATG  GACGCTTTAG  CTGTGGCTTT  CTTGTTTCTG   1980

AGACGGTCTC  GGTCTCGGTG  TGTTGCCCGG  GCTGGTCTCC  AACTTCTGGG  CTCAAGCGAT   2040

CCTCCCGGCT  CAGTCGCGTC  GACTTTAAAT  GCTTTATAAT  GCCCTTGCGA  GAAATGTGGC   2100

AGCCTGTCAT  CCTACTTAGT  GGTAGGAGAT  TGTTTCTATC  CAGAAGGGAC  ACTGCTGGTG   2160

GTATTTTAGT  ATAAATACTG  CCAGATGCGT  CCAAAACGTC  TGCATTAATA  ATGGCATCCT   2220

CCAGCAGTCC  GTTACCCTC   CACCAGTTCT  GAGACGGCCT  GACGGGTGAG  AGTGGTAACC   2280

CCTTCTAACC  GCGTTCGAAA  TACAGCCCTT  CAGCAGACGG  CGTTGATTTT  AAAGCATGTG   2340

TCTCCTGTCT  TCTAGTATGT  CCAAAATACT  AAAATGCGCC  GGCAATGAAG  ATATCATTAC   2400

ACTAAGGGCC  GAAGATAACG  CGGATACCTT  GGCGCTAGTA  TTTGAAGCAC  CAAGTAAGTC   2460

GTACCTTTTT  ACCGAGTCAC  GAAGCTACAG  GAAAATCAAA  ACTCTGTGTG  AGTAGAAACT   2520
```

-continued

```
CAAAAGCTAT CTGCGTTTCT TTTGGTAAGA CCAGGAGAAA GTTTCAGACT ATGAAATGAA      2580
GTTGATGGAT TTAGATGTTG AACAACTTGG AATTCCAGTG AGTATCAGTT TCTCATTGTA      2640
GAGAGTGCTG TACACAGGCA CGATAGTTAT GTCATAGAAT GTTTGTTTAT TTTACAGAC       2700
AGGGTCTTGG CTCTGTTGCC CAGGCTGGAG TGCAGTAGTG CCATATAGCT CTCTCTAACC      2760
TGGGATTCCT GGGCTCAAGC AGTCCTCTTG CCTTAGTCTC CTAAGTGGCT AGGAAGGACT      2820
ACGGGCCTGT CCCACCACAC CTGGCTAATT TTTTCATTT TTGTGTGTGG GACGTGGGGG       2880
CAGTCTAGCC AGGCTGGCTG GAACTCCTGG CCTCAAGTGA TCCTCCTCCG TCAAGATATG      2940
TTAATATAAT TTAAAGCCTA CTTCATAACA ACTTTTCTAG AAATATATCT ACTGGTGCAT      3000
GTTTCAAAGA GATGATTTTA GTATTTGGAT AGTTGTTCAC CACAAGTCTA ATAATCTCCA      3060
CAGGTTAAAT TTATTGTTTA TGCCAGTTGT CTATTGCAT TAACTTCCAT GAACTCTTTA       3120
AATTGTTCTC TAGAATGCTT GCTTTTTATT AATGAGGTTT TAAAGCTAGC TTGAGAGAAA      3180
TTTATCCAGG TTAGGTTATA AACACCAAAG GAGAGAAGAA ATGTTTGAAT GTTGAAAATG      3240
CCTAATATAT TCTCTTGCTT TCTTTTAGAA AGTGATTAGG CCTGCTTGCG CCATCATGAT      3300
TTCTGTGCCA TACTCTAATG TTCTCTTACT TTATCCCTGG AGGATGAGGA GGAGGAGGCT      3360
CTTGTTCCCT GGATGGTGCA TTTAATAGCC ATTTATTTTT TTGAGTGGAG TTTGTTAAGA      3420
AATTACGCAA GTCATATTTT AAAGTAATCA GAAAATATGA TTCTGAGTTG TTTAGGTGTT      3480
GCCTTTTAAG AAAGTGAGGG TGCCAAATCA TTAAATTTCT AACAATTAAC TTTTGGAAAA      3540
TTTTGTTCTT AATAGGAACA GGAGTACAGC TGTGTAGTAA AGATGCCTTC TGGTGAATTT      3600
GCACGTATAT GCCGAGATCT CAGCCATATT GGAGATGCTG TTGTAATTTC CTGTGCAAAA      3660
GACGGAGTGA AATTTTCTGC AAGTGGAGAA CTTGGAAATG GAAACATTAA ATTGTCACAG      3720
ACAAGTAATG TCGATAAAGA GGAGGAAGCT GTAAGTAGTT TTTAAGTAAA AAGAAAATAG      3780
TTTGAAGAGA ATTATAATAC TGCTTATTAG GTTAATTGCT AAAATTAAAA GTAGACAGAA      3840
TTGGATCCCA AGTAATTTCT GAAAATTGAG ATACTGTTGA AATCTGTGAA TGATTTATAA      3900
GTGTCATCCA ATTAGAATT ATATTTGCAA GAAGGGAATA CAAATTCAGC ACGTGTACAT       3960
ACCACAGCAA CAGTGGTTTA TGGATCAAGT CCACACCGGC TCTTAAGGGT AGGATTGGGA      4020
AGTTAGGCGT ATAACTTAGC TTCTGGAGAT ACTTACTCTC TTACCAAATA ATTGAGCATA      4080
GGACAGCAGC TCAATAGAAG GATATGTTAG GAGTAAAAGT CTACCTGTTT GGAGCACTTA      4140
TGTAATCCTA ATATAGCTTA CATGTTGTGG GTCCAATTGG TAGCCCATTT TAAAGGTGGA      4200
GAAGCAGGCT GAGCAACCTT AAGTGACAAT TTAGCCAAAG TCACAGGCTG TAGGAATCAA      4260
AGGTTAAACA GGAAGGAGAC TCTCACTAAG GCTAGAAAGC AGACTCCATG CAACTTTGAG      4320
AGTACCTAGA GAGACCCTTA TTTAACCAAA ATAGAAGAA CATAGCAAAA CCCCATCTCT       4380
CATAAAAATA TAAAAATTGA CCGGGTGATG AGTGGCGACA CACCTGTAAA CCCGACTACT      4440
GGAATGCATG AGATGGGAGA ATGACTTGAA CCGAGGAGGC GGAGGTTGCA GTGAGCCCAG      4500
ATCATGCCAC TCCCCTCCAG CCTGGGTGAC AGAGCAAGAT TCCATCTTAA ACAAACAAAA      4560
AAAACTCGCT AACCTGGGCA TAAATTAAAA CTTTGTAAAT CAAGGACAAA GGTCCTAAAC      4620
CTCATAACTT GCATTAGGAT TAAATACGGT AGCATTAAAG AGCTTAGCAT ATCTGTGTGT      4680
GGCATATTAT AAGCTTACAA TAAATACTAT ATATTGCTCT CTTGTCCCTT GAATGGGTAG      4740
TCAACATTTA GTTTAAATAA AGGTAAAATT CAGTTGAAAG GTTTTTTTTT AAATTAATAA      4800
AGTCTAGGAG CTGATTCTTT ATCTGTTTCC TGAATCACAT TTCCACTCCT GCCAACCTCG      4860
TTTTTTTCTT TTGCTGTTTT TCTTTGTTTT TGAGACAGGG CTTGCTCTGT GCCACCCAGG      4920
```

|  |  |  |  |  |  |
|---|---|---|---|---|---|
| CTGGAGTGCG | GTGGTGCAGT | CGGTTCACTA | CAGCCTCAAA | CTCCAGGGCT | TAAGTGATCC | 4980 |
| TCCTGCCTCA | GTTTCCCAAG | AGCCGGGACA | CAGGTGTGTG | CCAACACACT | AGCCTGGTTT | 5040 |
| CCCTAATTTC | ATTTTCCCCT | TGACCATTAC | AACTATTTGT | TGAAGAAATT | AGATCATTTA | 5100 |
| TTAGTTTCAG | AGTTTGGATT | TTACCTGATT | GCATTCCTGT | GTATCTAATA | ACCTCTACCT | 5160 |
| GTGTGTCCTA | CAGACTGGTA | GCTATAGCCT | GGAGCCTTGA | TATCAGGGTG | TTTTGTTTCG | 5220 |
| GGGGTGAGAG | AGCAAGAATA | TGGTGGTGGT | GTGTGTGCCT | CTAGTAGGAG | GCACAGGGTG | 5280 |
| TCTGGATGTG | TTTGCAATGT | TAGCAGCTAT | AAGTCATTGT | CTAGATCCAT | TAAGTCATTA | 5340 |
| ATTAGAGTTT | GCAGAGCTGA | AATTAATACG | TTTTATCACT | TATTGGCTGC | TTATTAGAAA | 5400 |
| ACTTCCATAA | GAAAAGCTTC | CCATTATATA | ATTTGGTTAT | CTAAATTATA | GCTACCAA | 5460 |
| AAGACAAAGG | CTAGATAATC | GAGTCTTTTT | GCATTTATGT | ATCAGTCTTC | AAAATTTTCA | 5520 |
| TAGCGTCCCT | CCAAAGTGAC | CAATACAAGT | GTTTGTGGGT | TTTTATAAAT | ATATAATGAG | 5580 |
| CTAATAGATT | GCAACTTTCT | TGATGTTTTT | CAATGATGAA | TCTTTTGTTT | TGTAGGTTAC | 5640 |
| CATAGAGATG | AATGAACCAG | TTCAACTAAC | TTTTGCACTG | AGGTACCTGA | ACTTCTTTAC | 5700 |
| AAAAGCCACT | CCACTCTCTT | CAACGGTGAC | ACTCAGTATG | TCTGCAGATG | TACCCCTTGG | 5760 |
| TAAGATAATA | AATTTGAACC | TTGTTTTGAT | GGTAGTCATA | TGTGATACAT | ACTCCTCAGT | 5820 |
| AATTAACCAT | CTTCCTGTCT | TTCAGTTGTA | GAGTATAAAA | TTGCGGATAT | GGGACACTTA | 5880 |
| AAATACTACT | TGGCTCCCAA | GATCGAGGAT | GAAGAAGGAT | CTTAGGCATT | CTTAAAATTC | 5940 |
| AAGAAAATAA | AACTAAGCTC | TTTGAGAACT | GCTTCTAAGA | TGCCAGCATA | TACTGAAGTC | 6000 |
| TTTTCTGTCA | CCAAATTTGT | ACCTCTAAGT | ACATATGTAG | ATATTGTTTT | CTGTAAATAA | 6060 |
| CCTATTTTTT | TTCTCTATTC | TCTCCAATTT | GTTTAAAGAA | TAAAGTCCAA | AGTCTGATCT | 6120 |
| GGTCTAGTTA | ACCTAGAAGT | ATTTTTGTCT | CTTAGAAATA | CTTGTGATTT | TTATAATACA | 6180 |
| AAAGGGTCTT | GACTCTAAAT | GCAGTTTTAA | GAATTGTTTT | TGAATTTAAA | TAAAGTTACT | 6240 |
| TGAATTTCAA | AGATCACAGG | GCAGTGTCTT | CATTTGACCA | GGACTGTTGA | AAGTATCCTA | 6300 |
| CTGAATTCCC | AGCTACAGTC | ACCCTTTGTT | CAAACTGTTC |  |  | 6340 |

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( v i ) ORIGINAL SOURCE:
        ( C ) INDIVIDUAL ISOLATE: Non-Human Anti-Sense
           Deoxynucleotide to c-myc #1

( x i ) SEQUENCE DESCRIPTION: SEQ ID NO:4:

CACGTTGAG GGGCAT                                               15

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (i i) MOLECULE TYPE: cDNA to mRNA (i i i) HYPOTHETICAL: NO (i v) ANTI-SENSE: YES (v i) ORIGINAL SOURCE:
    (C) INDIVIDUAL ISOLATE: Non-human Anti-sense DNA
        Deoxynucleotide to c-myc #2

(x i) SEQUENCE DESCRIPTION: SEQ ID NO:5:

CACGTTGAGG GGCATCGT 18

(2) INFORMATION FOR SEQ ID NO:6:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: cDNA to mRNA (i i i) HYPOTHETICAL: NO (i v) ANTI-SENSE: YES (v i) ORIGINAL SOURCE:
    (C) INDIVIDUAL ISOLATE: Non-Human Antisense
        Oligodeoxynucleotide to PCNA #1

(x i) SEQUENCE DESCRIPTION: SEQ ID NO:6:

CATCAGACAT ACCTCAAA 18

(2) INFORMATION FOR SEQ ID NO:7:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (i i) MOLECULE TYPE: cDNA to mRNA (i i i) HYPOTHETICAL: NO (i v) ANTI-SENSE: YES (v i) ORIGINAL SOURCE:
    (C) INDIVIDUAL ISOLATE: Non-Human Antisense
        Deoxyoligonucleotide to Cyclin B1 #1

(x i) SEQUENCE DESCRIPTION: SEQ ID NO:7:

ATGAGGGCCA TCCTAAT 17

(2) INFORMATION FOR SEQ ID NO:8:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (i i) MOLECULE TYPE: cDNA TO mRNA (i i i) HYPOTHETICAL: NO (i v) ANTI-SENSE: YES (v i) ORIGINAL SOURCE:
    (C) INDIVIDUAL ISOLATE: Non-human Antisense
        oligodeoxynucleotide to c-myc oligo #3

(x i) SEQUENCE DESCRIPTION: SEQ ID NO:8:

CGTTGAGGGG CATCG                                                          15

( 2 ) INFORMATION FOR SEQ ID NO:9:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( v i ) ORIGINAL SOURCE:
        ( C ) INDIVIDUAL ISOLATE: Non-human Antisense
              oligodeoxynucleotide to c-myc oligo #4

( x i ) SEQUENCE DESCRIPTION: SEQ ID NO:9:

GAAGCTCACG T                                                              11

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( v i ) ORIGINAL SOURCE:
        ( C ) INDIVIDUAL ISOLATE: Non-human Antisense
              oligodeoxynucleotide to PCNA #2

( x i ) SEQUENCE DESCRIPTION: SEQ ID NO:10:

TGCCTCAAAC ATGGT                                                          15

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: YES ( v i ) ORIGINAL SOURCE:
        ( C ) INDIVIDUAL ISOLATE: Non-Human Antisense
              Deoxyoligonucleotide to Cyclin B1 #2

( x i ) SEQUENCE DESCRIPTION: SEQ ID NO:11:

GCGCTCCGCG TCACCA                                                         16

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear

```
            ( i i ) MOLECULE TYPE: mRNA ( i i i ) HYPOTHETICAL: NO ( i v ) ANTI-SENSE: NO ( v i ) ORIGINAL SOURCE:
                    ( C ) INDIVIDUAL ISOLATE: Non-Human PCNA mRNA
                          target sequence ( x i ) SEQUENCE DESCRIPTION: SEQ ID NO:12:

GCCACCAUGU UUGAGGCACG CCUGAUC                                                           2 7

( 2 ) INFORMATION FOR SEQ ID NO:13:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i i ) MOLECULE TYPE: mRNA ( i i i ) HYPOTHETICAL: NO ( i v ) ANTI-SENSE: NO ( v i ) ORIGINAL SOURCE:
                    ( C ) INDIVIDUAL ISOLATE: Non-Human c- myc mRNA
                          target sequence ( x i ) SEQUENCE DESCRIPTION: SEQ ID NO:13:

ACGACGAUGC CCCUCAACGU GAGCUUC                                                           2 7
```

INHIBITION OF CELL PROLIFERATION USING ANTISENSE OLIGONUCLEOTIDES

This application is a continuation of application Ser. No. 07/821,415, filed Jan. 14, 1992 now abandoned.

BACKGROUND OF THE INVENTION

Coronary balloon angioplasty is a procedure whereby a catheter bearing an inflatable distal balloon is inserted into the arterial lumen and expanded. This procedure can be used to open stenotic regions in vessels such as those caused by arterial plaques and fatty deposits. This procedure is widely used on patients suffering from atherosclerosis. Presently, United States physicians perform over 400,000 coronary balloon angioplasties every year. Other types of mechanical procedures for opening stenoses within the vasculature use lasers or atherectomy devices to remove occlusions. Numerous similar procedures for mechanically opening stenoses are performed in heart valves (valvuloplasty) and peripheral vessels (peripheral angioplasty). Additional mechanical procedures include stent implantation and atherectomy.

Smooth muscle cell (SMC) proliferation of the vascular wall is a normal response to various pathophysiologic stimuli, including those associated with procedures for mechanically opening stenoses. If the proliferation is extensive, it could lead to restenosis following the procedure. In particular, as many as 50% of the patients undergoing successful coronary angioplasty can develop recurrent coronary artery obstructions over the next several weeks and months. The restenosis process predominantly consists of the proliferation of medial SMCs and the migration of these cells to the vascular subintima, where they continue to proliferate. Thus, considerable attention has been focused on developing interventions designed to inhibit the complex signaling cascade necessary for vascular SMCs to change their phenotype from their normally quiescent, contractile state, to one that will permit them to re-enter the cell cycle and proliferate causing restenosis of the arterial vessel. Normally quiescent cells which are stimulated to begin proliferating are known as activated cells. Activated SMCs are known to express multiple growth factors and proto-oncogenes.

Several different classes of pharmacologic agents have been employed, as yet unsuccessfully, to prevent the restenosis caused by SMC cell activation. The clinical approach used heretofore has involved the development of interventions that inhibit specific factors which act at the cell surface. These specific factors act through signal transduction pathways to lead to cell division. For example, when SMCs are activated, they express growth factors and cytokines such as PDGF, aFGF and bFGF (acidic and basic fibroblast growth factors), IL-1 (interleukin 1), IL-6, IGF-1 and 2 (insulin-like growth factor 1 and 2), and TGFβ (transforming growth factor beta). They also up-regulate receptors for PDGF, EGF (epidermal growth factor), FGF and IGF-1. The stimulation of such SMC surface receptors activates signaling pathways that lead to DNA synthesis and thereafter cell mitosis and proliferation.

One approach to inhibiting mitogens which act upon the cell surface involves the use of antibodies directed against such mitogens as PDGF (platelet derived growth factor) and bFGF (basic fibroblast growth factor). However, neither these antibodies, nor any other approaches to inhibiting mitogens which act upon the cell surface have been shown to be effective in inhibiting the proliferation of SMCs upon activation. Thus, there remains no currently available method for reliably controlling cell activation in SMCs.

One approach to inhibiting the translation of various gene products involves the use of antisense oligonucleotides complementary to the mRNA coding for the gene product. Antisense molecules have been used to study regulation of the extracellular matrix proteoglycans in SMCs (Dreher et al, *European Journal of Cell Biology* 54:1–9 (1991)). However, antisense molecules have not been used in connection with inhibiting the proliferation or migration of activated SMCs n vivo during restenosis or otherwise.

Many gene products essential for the cell-division-cycle (cdc) are known in the art. Examples of these gene products are proteins such as proliferating cell nuclear antigen (PCNA), c-myc, and cyclin $B_1$. However, many other such cdc gene products are known. These gene products exert their effect intracellularly to facilitate the movement of the cell through the cell cycle. Many of these products appear to have an essential role in the completion of the cycle.

Proliferating cell nuclear antigen (PCNA) is a nuclear protein active in the cdc. PCNA is required for leading strand DNA synthesis by DNA polymerase delta, which is part of the essential pathway for DNA replication. Consistent with PCNA's essential role in DNA replication are the findings that 1) expression of PCNA is very low in quiescent and senescent cells but increases 6- to 7-fold after stimulation by serum, PDGF, FGF, or EGF and 2) that an antisense oligodeoxynucleotide targeted to PCNA mRNA from the transformed murine cell line, 3T3, inhibits DNA synthesis.

The c-myc gene product is encoded by an immediate early response gene, the expression of which can be induced by various mitogens. C-myc expression is involved in the signal transduction pathways leading to cell division. Studies have demonstrated that proliferating cells have higher levels of c-myc mRNA and c-myc protein than do quiescent cells. Antibodies directed against the human c-myc protein are known to inhibit DNA synthesis in nuclei isolated from human cells. Conversely, constitutive expression of c-myc produced by gene transfer inhibits induced differentiation of several cell lines. Constitutive expression of c-myc predisposes transgenic mice to the development of tumors.

Some studies have suggested that the c-myc gene product may play a proliferative role in SMCs. Balloon de-endothelialization and injury of rat aortas is known to increase c-myc mRNA expression of vascular SMC prior to their subsequent proliferation and migration. Also, SMCs in culture proliferate when exposed to several mitogens, including PDGF, FGF, EGF, IGF-1 and to serum. Each of these mitogens has been found to be capable of increasing the expression in other cell lines of either c-myc protein, c-myc mRNA, or both. Additionally, blood serum has been found to increase c-myc mRNA levels in SMCs.

Harel-Bellan et al (*J. Immun.* 140; 2431–2435 (1988)) demonstrated that antisense oligonucleotides complementary to c-myc mRNA effectively inhibited the translation thereof in human T cells. These T cells were prevented from entering the S phase of cell division. Such antisense molecules have not heretofore been shown to be effective in inhibiting the proliferation of SMCs; nor have they been shown to be effective in inhibiting the migration of any cells.

Cyclin $B_1$ and cdc2 are other cdc gene products known to act in a crucial step of a dividing cell during the transition of that cell from $G_2$ to M. This step involves the activation of a protein-serine/threonine kinase, which is now known to be a complex of cdc2 and cyclin $B_1$. Although mRNA and protein levels of cdc2 are constant throughout the cell cycle, cyclin $B_1$ protein levels gradually increase through interphase and reach a peak at entry into M phase. The levels of cyclin $B_1$ fall abruptly during metaphase, a change responsible for moving the cell through and out of M phase. Mutations of the cyclin gene are known to cause cellular arrest in metaphase.

SUMMARY OF THE INVENTION

The current invention provides a method for blocking proliferation of a non-transformed cell in vivo or in vitro. In the present invention, we have made use of antisense oligonucleotides directed against cdc gene products to prevent unwanted cell proliferation in activated, non-transformed cells.

One aspect of the current invention is a method of inhibiting restenosis of a blood vessel in a mammal after mechanical treatment of the vessel to reduce a stenosis. This method involves contacting proliferating smooth muscle cells in the vessel with an antisense oligonucleotide, preferably a synthetic oligonucleotide, directed against cellular division cycle gene transcripts. The gene transcripts in one preferred embodiment of the current invention are, for example, cellular oncogene products such as c-myc, PCNA, or cyclin $B_1$. In this preferred example, the antisense oligonucleotides are used in an amount effective to inhibit translation of the cellular division cycle gene transcripts in the cell. In another embodiment of the current invention the oligonucleotide is an ODN and is, in yet another embodiment, chemically modified with phosphoramidate linkages in order to block exonucleolytic degradation. Another embodiment of the current invention uses an oligonucleotide which is a RNA molecule.

Another embodiment of the current invention is a method of inhibiting the growth of a proliferating SMC cell, which is preferably an activated, but non-transformed, cell derived from vascular tissue. This inhibition is preferably directed towards part of a tissue of a living organism, such as a mammal, by administering to the cell an antisense oligonucleotide directed against a cellular division cycle gene transcripts. The aforementioned cell is preferably capable of migrating from a first position in the organism to another position in the organism and, in one preferred embodiment, across a membrane barrier.

Another aspect of the current invention is a method of inhibiting stenosis of a blood vessel, or preferably an artery, in a mammal, by administering to the mammal an antisense oligonucleotide capable of inhibiting the growth of cells proliferating in the vessel. In one preferred embodiment the artery is a coronary artery, and in still another preferred embodiment of this method, the antisense oligonucleotide is directed to a cellular division cycle gene transcript, such as c-myc, PCNA, or cyclin $B_1$ in a concentration capable of being produced by the smooth muscle cells of the blood vessel in an amount effective to inhibit translation of the gene product in the cells. In yet another preferred embodiment, the antisense oligonucleotide is administered after treatment of the vessel for stenosis, wherein the treatment is procedure such as coronary balloon angioplasty. And still yet another preferred embodiment of the current method uses an oligonucleotide derived from a synthetic oligonucleotide and is preferably chemically modified with phosphoramidate linkages to block exonucleolytic degradation. In another preferred embodiment the oligonucleotide is an ODN, with still another embodiment being wherein the oligonucleotide is made of RNA.

One other preferred embodiment of the current invention is drawn to a method of inhibiting the growth of a mammalian smooth muscle cell, preferably non-transformed, by contacting the cell with an antisense oligonucleotide directed against a cellular division cycle gene transcript capable of being produced by the cell, in an amount effective to inhibit translation of the gene transcript in the cell. In one embodiment of this method the cell is in in vitro cell culture.

Still another embodiment of the current invention is an antisense oligonucleotide directed against cyclin $B_1$ with the preferred embodiment being an ODN. This antisense oligonucleotide is preferably a synthetic oligonucleotide and most preferably chemically modified with phosphoramidate linkages to block exonucleolytic degradation. Still another embodiment uses an oligonucleotide which contain RNA.

DETAILED DESCRIPTION OF THE INVENTION

Figure 1:
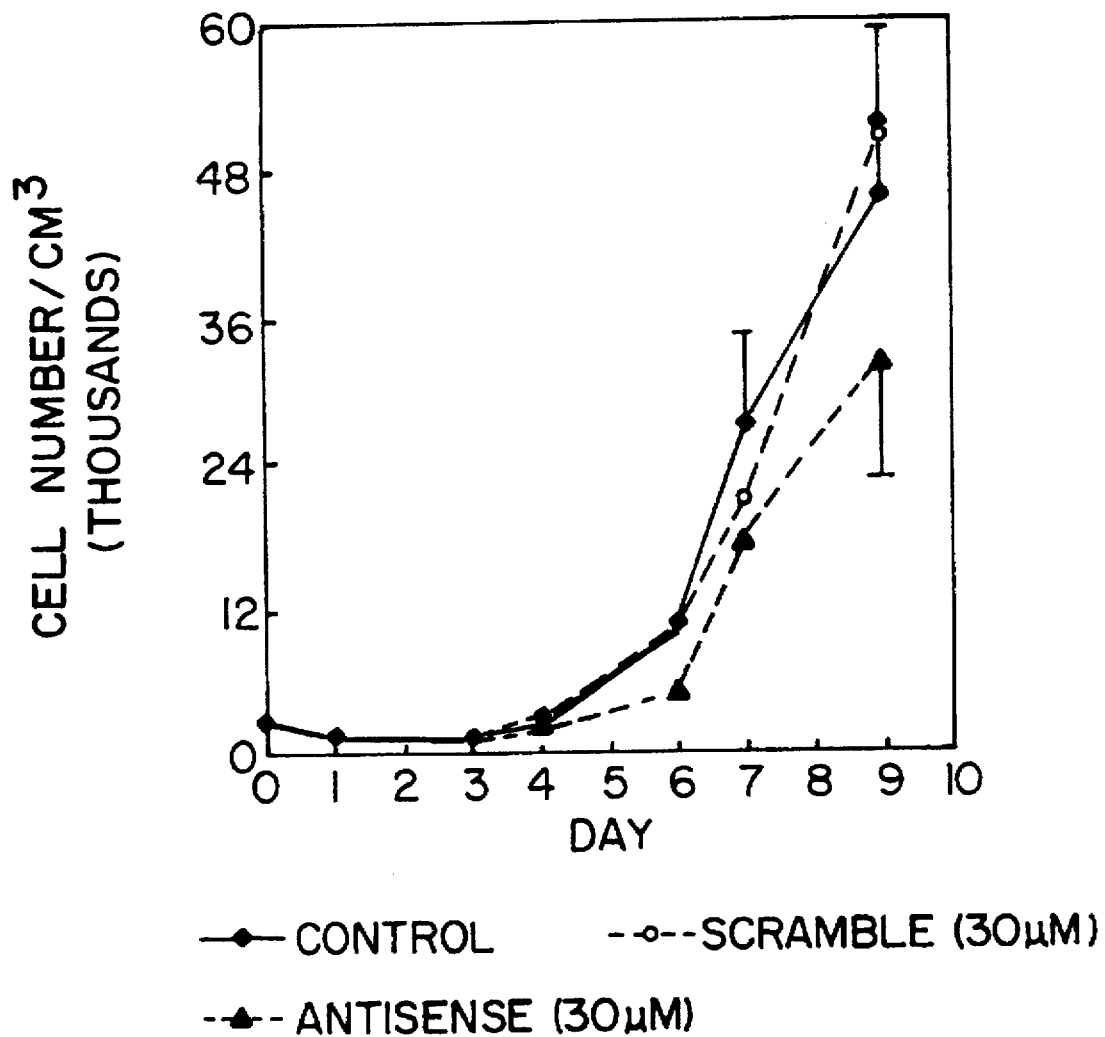
FIG. 1 is a line graph listing on the horizontal axis, the number of days of treatment with 30 micromolar of either antisense or scrambled antisense oligonucleotides directed against PCNA. The vertical axis depicts the number of cells. This graph shows stronger inhibition of cellular proliferation with PCNA antisense RNA than with scrambled oligonucleotide sequences.

The use of antisense strategies presents a theoretically simple tool to identify, with exquisite precision, the molecular mechanisms responsible for various cellular processes. It is based on the fact that each protein synthesized by a cell is encoded by a specific messenger mRNA (mRNA). If translation of a specific RNA is inhibited, the protein product derived from this translation will likewise be reduced. Oligonucleotide sequences, can therefore be designed to be complementary (antisense) to a specific target mRNA sequence and, because of this complementarity, it will bind to the target sequence thereby inhibiting translation of that specific mRNA. An antisense oligonucleotide complementary to a particular mRNA is referred to herein as being "directed against" the product of translation of that message. It is believed that an antisense oligonucleotide, by hybridizing to the RNA and forming a complex, blocks target mRNA ribosomal binding causing translational inhibition. Alternatively, the duplex that is formed by the sense and antisense molecules may be easier to degrade. Other theories describe complexes that antisense RNA could form with complementary DNA to inhibit mRNA transcription. Thus, an antisense oligonucleotide might inhibit the translation of a given gene product by either directly inhibiting translation or through inhibition of transcription.

Antisense oligodeoxynucleotides (ODNs) directed to the mRNA of c-myc can inhibit the proliferation of the transformed cell line HL60 and can also inhibit mitogen stimulated DNA synthesis of another transformed cell line derived from lymphocytes. However, antisense oligonucleotides have not been used to block the proliferation of activated cells nor of any cells derived from the hematopoietic system.

We believe that inhibiting the various mitogens which act on the cell surface is not likely to provide an effective strategy for preventing SMC proliferation due to the redundancy of the signal transduction pathways triggered by cell surface events. This is because if one such pathway is effectively inhibited, alternative pathways might still produce substantial SMC proliferation. Thus, we looked for strategies of inhibiting SMC proliferation that avoided this redundancy problem.

In this regard, we have discovered that proliferation and migration of SMCs, both in vivo and in vitro, can be inhibited through the use of antisense oligonucleotides directly capable of inhibiting cellular growth. One aspect of this discovery involves the use of antisense oligonucleotides directed against cdc gene products.

As discussed above, many of these cdc gene products, such as c-myc, PCNA, cdc2 and cyclin $B_1$, are required for the cell to complete its cycle. Our discovery includes the use of antisense oligonucleotides directed against any of these required gene products as effective inhibitors of cellular proliferation and migration of activated SMCs.

In the practice of a preferred embodiment of the present invention, the antisense oligonucleotide is used in preventing the proliferation of smooth muscle cells. This embodiment is particularly useful in the treatment of restenosis following coronary angioplasty. The treatment involves contacting the cells with an antisense oligonucleotide capable of inhibiting SMC proliferation.

PRODUCTION OF ANTISENSE OLIGONUCLEOTIDES

Thus, we specifically evaluated the ability of antisense oligonucleotides directed against PCNA and c-myc, and also evaluated a molecule directed against cyclin $B_1$, to prevent translation of the specific gene product in proliferating SMCs. We first determined that stable, antisense oligonucleotides directed against these cdc gene products could be produced. These experiments are shown below in Examples 1-2.

EXAMPLE 1
Synthesis of Oligomers and Selection of mRNA Sequence Targets

The methoxyethylamine 3' end-cap oligodeoxynucleotides were prepared on a Biosearch 8750 DNA synthesizer, using standard H-phosphonate chemistry on controlled pore glass. The 15 or 18-base oligodeoxynucleotides were purified via DMT-on purification on a semi-prep Dynamax C-4 300A column. A secondary DMT-off purification was then performed on the same column. Finally, the oligomers were desalted over a Pharmacia NAP-25 column, converted to the sodium form via Biorad AC 50W-X8 (Na+) 200–400 mesh polyprep column, and then passed over another NAP-25 column. The antisense oligos and their controls, which contained the same bases but in scrambled sequence, were obtained from Dr. N. Bischofberger (Gilead Sciences, Foster City, Calif.). Lyophilized oligomers (ODNs) used in cell experiments were dissolved in PBS (1 mM stock) and sterile filtered with Millipore 0.2 micrometer disks.

Using the method of Example 1, we prepared antisense ODNs directed against PCNA and c-myc. The sequence we targeted for antisense inhibitory studies on the c-myc gene was a 27 base region of the corresponding mRNA spanning the AUG translation initiation codon (Sequence ID No. 13). The sequence we targeted to study on the PCNA gene was a 27 base pair region of the corresponding mRNA also spanning the AUG initiation codon (Sequence ID No. 12). While the present invention is not limited to such sequences, antisense oligonucleotides directed against the initiation codon region of the mRNA are one type of antisense molecule believed to effectively inhibit translation of the resulting gene product. Other effective antisense molecules can be specifically targeted against the opposite end of the mRNA.

The sequences of the antisense ODN we used directed against PCNA are listed as Sequence ID Nos. 6 and 10. The ODNs directed against c-myc are listed as Sequence ID Nos. 4, 5, 8, and 9. We have also identified two putative antisense oligomers directed against Cyclin $B_1$, which are listed as Sequence ID Nos. 7 and 11. These anti-cyclin $B_1$ sequences are believed effective in inhibiting the proliferation of SMCs.

The sequences identified for PCNA and for c-myc are representative non-human laboratory examples of those that have been tested against their respective RNA targets, and should not be interpreted as the only antisense sequences capable of inhibiting the resultant gene translation. The preferred antisense sequences are derived from the human cdc genes, and are effective in inhibiting the proliferation of human SMCs.

The complete human DNA sequences of c-myc, Cyclin $B_1$, and PCNA are listed as Sequence ID Nos. 1, 2, and 3 respectively. Potential target antisense oligonucleotide sequences for inhibiting translation of the human gene products can be readily derived from these DNA sequences by those of ordinary skill in the art.

Having determined that antisense oligonucleotides directed against cdc gene products could be successfully produced, we tested the stability of these oligonucleotides using a method shown in Example 2.

EXAMPLE 2
Determination of Oligomer Stability

Smooth muscle cells were grown in medium 199 supplemented with 10% fetal bovine serum and glutamine (all from Biofluids, Gaithersburg, Md.). We added ODNs to a final concentration of 30, 60 or 100 micromolar. Aliquots (20 microliters of ODN-containing media were removed at 30 min, 6 h, 24 h, 48 h, 72 h and 96 h, run on a 20% polyacrylamide, 5M urea minigel (Sepragel, National Diagnostics) at 20 mA for 3–4 hours and developed with Stains-All (Fluka, Ronconcoma, N.Y.) according to the manufacturer's instructions. The 3' end-capped 18-base oligomer (100 micromolar final concentration) was stable in medium for 72 hours; At 96 h the oligo was degraded by about 80%.

Example 2 shows that the oligonucleotides were stable for over 72 hours. This showed us that the oligonucleotides would be stable in the medium for enough time to be taken up by the smooth muscle cells.

INHIBITION OF SMOOTH MUSCLE CELL PROLIFERATION

We grew smooth muscle cells in culture in order to provide a model system in which to study the ability of antisense oligonucleotides to prevent cell proliferation. We wanted to study both cells growing exponentially and quiescent cells. The method of growth we used for both of these types of cell cultures is disclosed below in Example 3. However, a great variety of methods of cell culture will be known to those of ordinary skill in the art.

EXAMPLE 3
Cell Culture

Vascular smooth muscle cells (SMC) were isolated from the thoracic aortas of Sprague-Dawley rats or new Zealand white rabbits by enzymatic digestion or by explants of minced medial tissue. Briefly, SMCs were seeded (day 0) at 5000 cells/cm$^2$ in M199 and 10% FBS in 96-well plates for 24 h. The medium was then changed (day 1) to M199 and 0.5% FBS for 48 h. On day 3 the medium was replaced with M199/10% FBS containing 10, 30, 60 or 100 micromolar of either antisense, scrambled sequence control, or equal volumes of PBS, each in triplicate wells. Serum was replenished every 48 h and cells were grown for 10 days without medium change. In other protocols, medium and oligomers were removed twice (on day 3 and on day 7). We also experimented by adding the oligos on day 1 or on day 2 of the experiment. The various protocols gave similar results. At first, sister cultures were trypsinized and counted daily with an Elzone particle counter. In later experiments counts were taken on days 1, 3, 6 and 9.

The cultures described in Example 3 were used in a variety of experiments to determine the ability of antisense oligonucleotides to inhibit SMC proliferation. Our strategy of inhibiting SMC proliferation made use of antisense ODNs that were complementary to a corresponding target sequence of the mRNA encoding either PCNA or c-myc. Using this approach, we found that inhibition of both of these factors was capable of preventing SMCs from proceeding through the cell cycle and proliferating.

PCNA Studies

We evaluated the ability of the anti-PCNA ODNs to inhibit the proliferation and migration of SMCs. Example 4 is provided as an example of a study clearly showing the effectiveness of the antisense molecules in inhibiting SMC cell proliferation.

EXAMPLE 4
Growth Inhibition of SMCs by Anti-PCNA Oligomer

We added the antisense ODN directed against PCNA (Sequence ID No. 6) to the SMC culture of Example 3 at day 6. Significant growth inhibitory effects of anti-PCNA oligomer, as assessed by cell count, were apparent at 48–72 h after adding the antisense ODN (Seq. ID No. 6) to the SMC culture of Example 3 (day 6). In contrast, results after treatment with scrambled sequence ODN at the same concentration (100 micromolar) were not different from cell counts of SMC treated with PBS. Medium and oligomers were replenished after 72 h and again, an antiproliferative effect by antisense ODN is demonstrated in FIG. 3 after an additional 24 h (day 7) and 72 h (day 9). Concentrations of 100 micromolar appear to have been necessary to obtain maximal inhibition. Also, the effect of antisense is more pronounced on day 5, when SMC are very sparse.

FIG. 1 shows data from additional experiments performed using the method of Example 4. In these experiments, the concentration of the antisense ODN was limited to only 30 micromolar, and two controls were provided: PBS (control) and a scrambled sequence containing the same nucleotide content as Sequence ID No. 6. FIG. 1 shows that Sequence ID No. 6, targeted against rat PCNA to a sequence beginning at the second codon thereof, decreased SMC growth in a concentration-related manner (with a maximal inhibition of 50%) when compared to controls treated with either the scrambled sequence oligomer or with PBS.

To demonstrate that the effect of the antisense ODN is reversible, SMCs treated for 9 days were washed with PBS twice and fresh medium containing 10% FBS was then added. Thereafter, triplicate wells were harvested and counted daily. After 48 h all wells reached a density of 100,000 per cm$^2$ (confluence).

Thus, the results of Example 4 clearly show that antisense ODNs directed against PCNA are capable of reversibly inhibiting the proliferation of SMCs. To further ascertain that this effect was not due to general toxicity, we performed a Western blot experiment, as seen in Example 5, with monoclonal antibodies to actin.

EXAMPLE 5
Western Blot Analysis

SMCs were seeded at 5000/cm$^2$ in T75 flasks and grown in 10% FBS/M199 until cell density reached 35–40,000/cm$^2$. Parallel cultures were synchronized in one of two ways.

1) Serum starvation. For this protocol oligomers or PBS were added to the SMC after they had been serum-starved for 52 h with 0.5% FBS: 20 h later cells were stimulated with 15% FBs and incubated for another 20 h.

2) Double thymidine block. SMC synchronized via double thymidine block at a final concentration of 5 mM (Sigma, cell culture grade) for 24 h, washing out the thymidine, adding M199/10% FBS and ODNs or PBS for 15 h, then adding thymidine for another 24 h were treated with ODNs (Anti-PCNA, Sequence ID No. 6) or PBS after washing out the first thymidine dose: the oligos were added together with M199/10% FBS for 16 h. The second dose of thymidine was then added and the cells were incubated for an additional 24 h. Thus, the SMC were treated with ODNs for 40 h. We had first determined by immunofluorescence staining that nuclear staining for PCNA was maximal 1 to 3 hours after the second thymidine release, at which time 80% of the serum-stimulated cells were positive, whereas 4.5 h later a marked decrease in label was apparent. The SMC were therefore incubated in M199/10% FBS for 1–3 hours after thymidine was washed out the second time.

For both types of synchronization, cells were trypsinized, flash-frozen in liquid nitrogen, and incubating them in lysis buffer (0.01M Tris-HCl pH 7.5, 0.144M NaCl, 0.5% NP-40, 0.5% SDS, 0.1% Aprotinin and 1 mM phenylmethylsulphonylfluoride; (1×10$^6$ cells/20 microliters buffer) for 30 min on ice (vortexed every 10 min.). The lysates were centrifuged at 10,000 g for 10 min and subjected to 4–20% SDS-PAGE at 20 mA for 2.5 hours. Each well was loaded with approximately 20 microliters (100 micrograms of protein, BCA Kit, Pierce, Rockford, Ill.) of the samples (gels from Enprotech). The proteins were transferred for 90 min at 100 V in a Polyblot (American Bionetics, Hayward, Calif.), using the buffers specified by the manufacturer.

Immunoblotting was performed using monoclonal antibodies IgM (Coulter, Hialeah, Fla.) or IgG (Boehringer Mannheim, Indianapolis, Ind.), each at dilutions of 1:1000. The blots were incubated overnight with the anti-PCNA or antibodies and then with AP-conjugated secondary antibodies and substrates supplied with the Biorad kit. (Immunlite kit, Biorad, Richmond, Calif.). One ng PCNA protein purified from calf thymus was used as a standard and run in lane 4. Finally, the blots were exposed to Kodak XAR 2 film for 15 to 30 seconds at 22° C.

Figure 2:
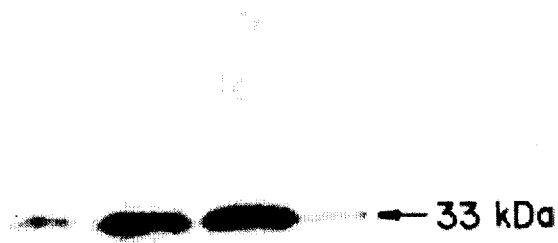
FIG. 2 is a Western Blot showing the effect of antisense ODNs directed against PCNA on levels of PCNA in cell lysates.

The resulting immunoblot is shown in FIG. 2. One ng PCNA was easily detectable as seen in lane 4 of FIG. 2. Lane 1 shows the lysates from the ODN treated cells. Lanes 2 and 3 show the PBS and scrambled ODN sequences, respectively. The immunoblots show a 50–75% decrease in the level of PCNA protein in synchronized SMC after 40 hours of incubation with 100 micromolar antisense oligomer. There was no apparent decrease in either of the controls; i.e., those exposed to scrambled ODN or those exposed to PBS. The results were similar whether cells were synchronized by thymidine block or by serum deprivation.

Thus, Example 5 provides further indication that SMC proliferation had been effectively blocked through antisense ODNs directed against PCNA. We also conducted studies on indirect immunofluorescence using an anti-PCNA antibody to show that PCNA levels were decreased in cells by this antisense molecule. The methods for these studies are shown in Example 6.

EXAMPLE 6
Indirect Immunofluorescence

We confirmed by immunocytochemical methods that the inducible form of PCNA was detectable in serum-stimulated SMCs. Smooth muscle cells were seeded at 5000/cm$_2$ in 4-well chamber-slides for 24 h. The growth medium (M199, 10% FBS) was then replaced and the SMC were incubated for 72 h with M199, 0.5% FBS and 100 micromolar anti-PCNA antisense or scrambled ODNs. After treatment with 10% FBS for 24 h, the cells were rinsed with PBS and stained as described by Kurki et al (*J. Immunological Methods* 109:49–59 (1988)), the disclosure of which is hereby incorporated by reference. Briefly, SMCs were fixed with 1% paraformaldehyde/PBS for 2 min at 22° followed by 10 min postfixation with absolute methanol at −20° C. The cells were then incubated with 10 microgram/ml monoclonal anti-PCNA IgM or 25 microgram/ml IgG for 2 h and labeled with 20 micrograms/ml FITC-conjugated, affinity-purified anti-mouse IgA+IgM+IgG (Kirkegaard & Perry, Gaithersburg, Md.) for 30 min. For microscopic analysis the SMC were mounted in 10% p-phenylenediamine/glycerol. Starved quiescent SMC and cells either lacking treatment with primary antibodies or incubated with irrelevant antibodies served as negative controls.

The results were strikingly similar to those published for other normal cells. Quiescent SMCs from Example 3 did not show nuclear staining with 19F4 anti-PCNA antibody, whereas the nuclei of serum-stimulated SMCs from Example 3 were clearly labeled, displaying a punctate pattern 14–20 h after addition of 10% serum. Previous experiments have shown that in unsynchronized exponentially growing cells, different nuclei were stained with dissimilar intensities, according to their positions in the cell cycle. In contrast, more than 80% of the SMC nuclei of synchronized cells were stained with similar intensity. Mouse myeloma protein used in the same concentrations as the anti-PCNA antibodies, or omission of primary antibodies, gave negative results. SMCs treated with antisense ODNs showed weakly stained nuclei in contrast to the intensely stained control cells. These results combined with those derived from the Western Blot showing that our antisense oligomer directed against PCNA mRNA inhibits the expression of PCNA, show that inhibiting PCNA production is an effective strategy for inhibiting SMC proliferation.

C-myc Studies

We also employed antisense oligodeoxynucleotides (ODNs) directed against c-myc in inhibiting the proliferation of SMCs. The oligodeoxynucleotides we used were chemically modified at the two terminal 3' phosphates with phosphoramidate linkages to block exonucleolytic degradation. Five antisense ODNs were used in this experiment. These modified ODNs were stable in cell culture medium for at least 5 days. Two of the 4 antisense ODNs directed against c-myc (Sequence ID Nos. 4 and 5), which were targeted to the region of the initiation codon of c-myc mRNA, inhibited SMC proliferation in a concentration-dependent manner in a system similar to that of Example 4. Maximal inhibition was 50% with an ID50 at 50 uM. However, ODNs with the same nucleotides as the 2 active ODNs, but with a scrambled sequence, had no such effect. The remaining two anti-c-myc ODNs had no significant effect on SMC proliferation.

The 15-mer ODN against c-myc (Sequence ID No. 4) that was complementary to the first five codons effectively inhibited SMC proliferation and expression of c-myc protein. Another 18-mer ODN, whose target began three bases 5' to the initiation codon of the c-myc gene (Sequence ID No. 5), also effectively inhibited SMC proliferation. However, only small shifts in the target sequences led to a total inability of the antisense ODNs to inhibit SMC proliferation.

There are, of course, many portions of gene sequences that can be potentially targeted for antisense therapy. The present invention includes the use of all sequences that can be used as antisense molecules to inhibit the growth of activated, non-transformed cells, such as through inhibiting the translation of cdc gene products. The determination of the proper sequences to target is always an important consideration when dealing with antisense strategies for inhibiting gene expression. Our results demonstrate the critical influence of the precise sequences that are being targeted on determining whether or not gene expression is effectively inhibited.

The foregoing target dependence may be related to secondary structures of the mRNA strand that could interfere with hybridization of the ODN to the corresponding mRNA target. Activity could also be influenced by changes in cellular uptake efficiency, or by the ability of the ribosome to read through the particular duplex formed by the mRNA and its complementary ODN.

Figure 3:
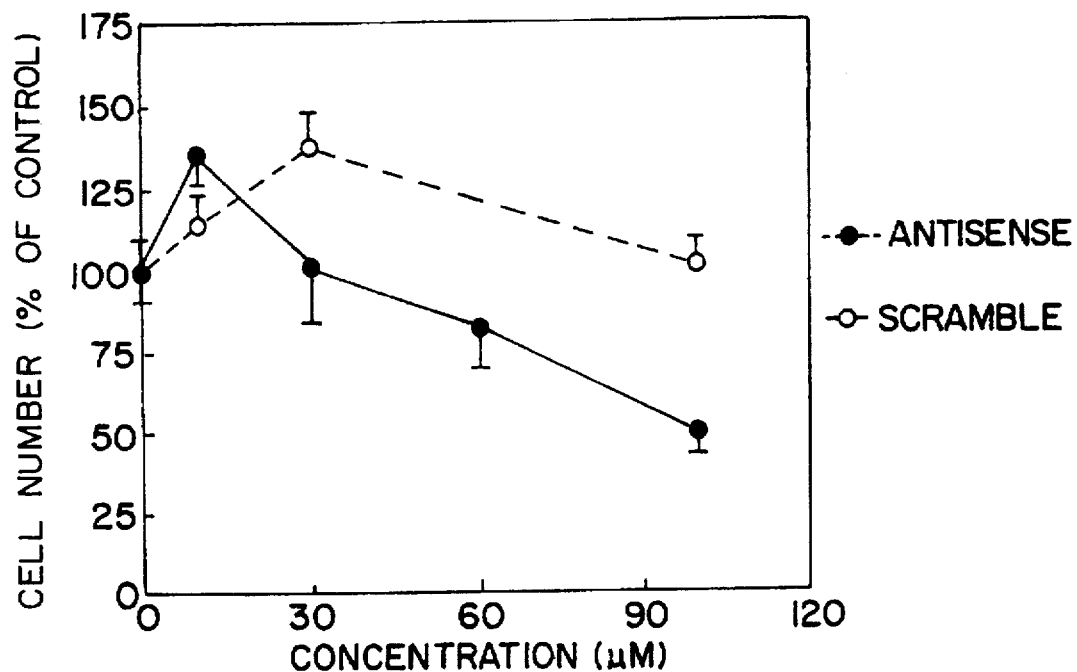
FIG. 3 is a line graph listing on the horizontal axis, the molar concentration of c-myc antisense molecules, and on the vertical axis, the number of transfected cells. This graph shows stronger inhibition of cellular proliferation with increasing concentration of c-myc antisense RNA than with scrambled oligonucleotide sequences.

FIG. 3 shows the results of one experiment performed using a method similar to that for Example 4, substituting an anti-c-myc ODN for the ODN directed against PCNA. A scrambled sequence was used as a control. It can be seen that the antisense ODN directed against c-myc decreased cell number in a concentration dependent manner. Whereas, the scrambled sequence did not appear to have this effect.

Both SMC migration and SMC proliferation are important components of the restenosis process after arterial angioplasty. Thus, we also studied the inhibition of cell migration caused by antisense ODN directed against c-myc. To determine whether c-myc is involved in a signal transduction pathway leading to SMC proliferation and migration, we investigated the effects of an antisense ODN (18 mer) targeted to c-myc mRNA (Sequence ID No. 5) in an in vitro model for cell migration known as the Boyden chamber method. This method is shown in Example 7.

EXAMPLE 7
Inhibition of SMC Migration by ODN Directed Against c-myc

The method we employed to investigate SMC migration is described by G. A. A. Ferns et al (*Growth Factors*, 3:315–324 (1990)), the disclosure of which is hereby incorporated by reference. In studies to define the model, we found that the greatest stimulation of SMC migration occurred when 10% FBS was added to the lower chamber of the apparatus. We therefore employed this model to test the effect of antisense. We discovered that the antisense ODN to c-myc consistently decreased SMC migration in a concentration-dependent manner. The scrambled ODN control exerted no effect on migration. The inhibitory effect was most prominent when the antisense ODN was added to the lower, in contrast to the upper, chamber. Maximal inhibition of migration was 90%, with an $ID_{50}$ of 1 micrometer.

Figure 4:
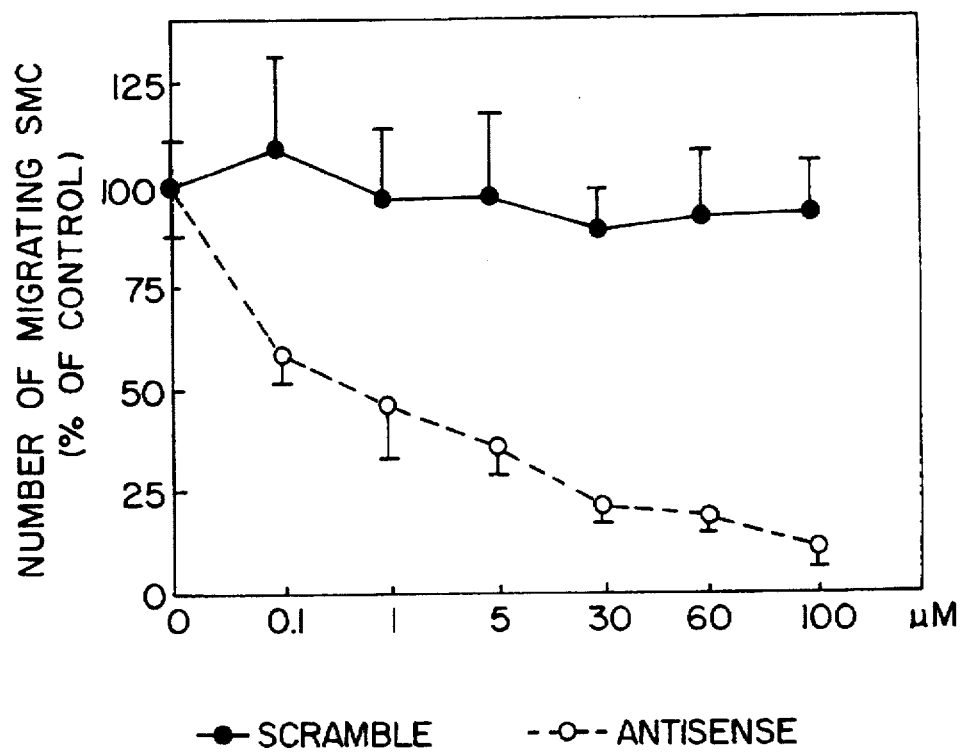
FIG. 4 is a line graph listing on the horizontal axis, the concentration of c-myc antisense molecules, and on the vertical axis the number of migrating SMCs. The antisense treated cells have a strongly inhibited migration compared to the scrambled control.

The foregoing results are shown graphically in FIG. 4. Thus, the results of Example 7 show the dramatic effect on SMC migration produced by the ODNs directed against c-myc.

Although the signal transduction pathways modulating SMC proliferation and migration are unknown, from the results of the studies of Example 7, the modulation of migration appears to be more sensitive to inhibition by c-myc antisense oligonucleotide than that of proliferation. Thus, lower threshold inhibitory concentrations and greater maximal inhibitory activity were found in the migration versus the proliferation experiments. The maximal inhibition of proliferation achieved by the antisense ODNs we employed was 50%, while maximal inhibition of migration was over 90%.

To determine whether the inhibitory effects on SMC proliferation and migration of antisense ODN directed against c-myc were associated with a specific effect on c-myc expression, immunohistochemical staining and Western blot analysis were performed using antisense oligonucleotide directed against c-myc in a manner similar to that shown in Examples 5 and 6 for antisense ODN directed against PCNA. Quiescent cells had lower levels of immunoreactive c-myc protein than did the rapidly proliferating cells, both by immunohistochemical staining and by Western blot analysis. Antisense RNA diminished the amount of immunoreactive c-myc protein present in these rapidly proliferating cells, while the scrambled ODNs had no effect. This was found when the intensity of nuclear immunostaining was assessed by the blinded reading of three individual observers, or when the amount of expressed protein was estimated by Western analysis as in Example 5. The latter observations were confirmed by laser densitometry.

Figure 5A:
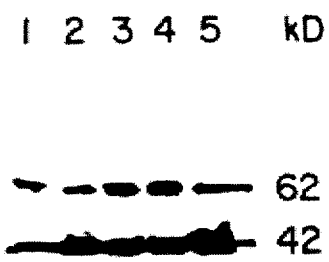
FIGS. 5 (A and B) is a western blot comparing cells that were untreated, treated with scramble control oligonucleotides, or treated with antisense oligonucleotides directed toward reducing c-myc translation. This blot shows lower levels of immunoreactive c-myc in the cells treated with antisense RNA when compared to the controls.
Figure 5B:
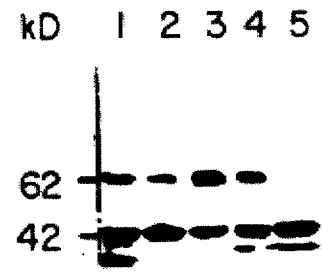

FIG. 5 shows the results of two Western Blots comparing the effect of ODNs directed against c-myc on activated HL-60 (Panel A) cells and SMCs (panel B). Each lane contained cell lysates, lane 1 of each panel showed unactivated cells, lane 2 showed quiescent cells activated with 0.5% FBS, lane 3 showed cells activated with 10% FBS, lane 4 showed activated cells treated with scrambled ODNs and lane 5 showed activated cells treated with ODNs directed against c-myc. It can be seen that activation with 10% FBS increased levels of c-myc, seen at 62 kD and that antisense ODN directed against c-myc reduces levels of c-myc. The level of c-myc was much more efficiently inhibited in SMCs than HL60 cells.

The antibody used in the Western Blots of FIG. 5 is cross-reactive with both actin and c-myc. Thus, actin is shown in these Blots as a 62 kD protein. The data from FIG. 5 demonstrate that equivalent amounts of actin are present in $10^6$ SMCs treated with PBS, scrambled ODN or with antisense ODN. Accordingly, the effect on SMC proliferation seen by antisense ODNs directed against PCNA or c-myc is not believed to be caused by general toxicity since actin levels are consistent in every lane.

We believe that the diminished proliferation and migration effects caused by antisense ODN directed against c-myc are due to decreased translation of the c-myc gene product caused by the antisense ODN binding to the c-myc message. This conclusion is based on several observations: 1) an ODN with identical bases as the antisense molecule, but placed in random sequence (scrambled control), had no inhibitory effects on SMC proliferation; 2) expression of c-myc protein was reduced by the antisense ODN, as demonstrated by Western blot analysis and by immunohistochemical techniques, despite the fact that there appeared to be no generalized depression of protein synthesis, as assessed by actin gene expression. The mechanisms by which c-myc influences cell proliferation and cell migration are unknown. However, two domains in the carboxyl terminus of c-myc are involved in DNA binding.

It has recently been shown by others that the N-terminal domain of the c-myc protein mediates binding to the retinoblastoma gene product, pRb. Since Rb is an inhibitory gene, the fact that c-myc can bind pRb (while it cannot bind to a mutant Rb protein from a human tumor cell line) suggests that c-myc may stimulate cell proliferation, at least in part, by inactivating the inhibitory gene product of Rb.

Cyclin $B_1$ Studies

As noted above in the Background of Invention section hereof, cyclin $B_1$ plays a pivotal role in the progress of a proliferating cell through the cell cycle. Levels of cyclin $B_1$ gradually increase through interphase and reach a peak at entry into M phase. Cyclin $B_1$ levels then fall abruptly during metaphase. It has been found that mutations of the cyclin gene lead to arrest of the cell in metaphase. It is believed that the change in cyclin gene product levels are responsible for moving the cell through and out of M phase. Because entry of the cell into M phase is distal in the cell cycle pathway, we believe that inhibition of cyclin $B_1$ gene product translation will markedly decrease SMC proliferation.

Thus, we have cloned the cDNA of rabbit cyclin $B_1$ in order to determine whether inhibiting the expression of this gene product with antisense oligonucleotides inhibits SMC proliferation. There is marked conservation of a region known as the cyclin box amongst several species, including between rabbit and humans. Another conserved region, known as the destruction box, appears to be both necessary and sufficient for mitotic proteolysis of proteins containing the amino acids coded by this region. Putative ODNs directed against cyclin $B_1$ are disclosed as Sequence ID Nos. 7 and 11. Those having ordinary skill in the art should have no difficulty identifying ODNs complementary to different portions of the cyclin $B_1$ mRNA which can be successfully used to inhibit translation of the cyclin $B_1$ gene product, and consequently which will inhibit SMC proliferation and migration.

In order to use the antisense oligonucleotides directed against cyclin $B_1$ in accordance with the present invention, the oligonucleotides can be prepared and used according to the procedures described above in connection with c-myc and PCNA. Similar procedures can also be used for other cdc gene products, such as cdc2.

Methods of Treatment

As discussed above, the present invention includes the use of antisense oligonucleotides in therapy directed against the proliferation of non-transformed cells. For example, the inhibition of SMC proliferation through use of these antisense molecules can provide beneficial therapy in inhibiting restenosis following arterial angioplasty. These therapeutic methods require that targeted cells be contacted with the particular therapeutic antisense molecule. Many methodologies for contacting cells with nucleotide sequences in vivo will suggest themselves to one of ordinary skill in the art.

Liposome Methodologies

One strategy for delivering antisense oligonucleotides to targeted cells involves encapsulating the therapeutic molecules in liposomes, such as cationic liposomes. These liposomes are known to provide a shield against nucleotide degradation in vivo and can be targeted to specific areas of the body at which point they slowly release their contents. For a detailed review of methodologies relating to liposome preparation see *Liposome Technology* by Gregoriadis (CFC Press, NY 1984), *Liposomes* by Ostro (Marcek Dekker, 1987), and a review by Lichtenberg, et al. (*Methods Biochem. Anal.* 33:337–462, 1988), the disclosures of each of these references being hereby incorporated by reference.

The first step in cationic lipid mediated transfection or polyanion delivery involves the spontaneous formation of a complex between cationic lipid vessels and the polyanionic macromolecules such as RNA. This step is mediated by strong, cooperative ionic interactions between the positively charged groups on the lipid vessels and the negatively charged phosphate groups on the antisense RNA When sufficient quantity of cationic lipid is used, the resulting complexes have a net positive charge and therefore will attach spontaneously to cell surfaces. Cell surface attachment is followed immediately by fusion of the cellular and liposomal membranes thus allowing material in the complexes to escape degradation from lysosomal compartments permitting direct delivery into the cytoplasm.

The active component of these fusogenic liposomes is a bilayer forming synthetic cationic lipid, such as DORI, DORIE or DOTMA. The fusogenic capacity of these vessels as well as the complexes they form can be somewhat controlled by the choice of neutral lipid into the liposome membrane. Alpha-tocopherol (Sigma, St. Louis, Mo.) can be added to the lipid bilayer to prevent oxidative degradation. Formulation buffers need to be of low ionic strength to avoid shielding of the charges. Formulation methodologies that result in unilamellar vessels of the smallest possible size are preferred in order to provide the largest possible cationic surface to ensure that most efficient complexation with the antisense RNA and subsequent fusion with and delivery to the target cells. Sonication or microfluidization are well described liposome formulation methodologies that fulfill these criteria.

The preparation of sonicated cationic liposomes is described by Felgner, et al. (*Proc. Natl. Acad. Sci.* 84:7413–7417 (1987)), the disclosure of which is incorporated herein by reference.

Encapsulation or incorporation of bioactive molecules into cationic liposomes enables their "direct" delivery to the membranes or the cytoplasm of target cells, similarly to transfection.

In one embodiment of the present invention, liposomes containing antisense oligonucleotides effective in inhibiting SMC cell proliferation can be administered by cardiac catheter to the SMC proliferation site. After injection at the proper site, these antisense containing vessels are expected to fuse to the SMC cell wall, and thereby inhibit SMC proliferation.

This liposome method also includes transfecting the proliferating cells with, for example, liposomes containing plasmids containing DNA which codes for antisense RNA. These plasmids, upon introduction into the cell, would begin transcribing antisense RNA directed against a cdc gene product, thereby inhibiting proliferation. Other delivery systems are being explored which include biodegradable stents and biodegradable microspheres.

Direct Injection

Another method of inserting exogenous nucleotide sequences into a cell in vivo simply requires injecting those sequences in or adjacent to the cells. At the proper concentration, proliferating cells will take up and express exogenous oligonucleotides. These nucleotide sequences could be, for example, antisense directed towards mRNA. Alternatively, plasmid DNA which contains a gene coding for antisense oligonucleotide could be used. The nucleotide sequences are administered in a suitable buffer or carrier solution, which will be known to those of skill in the art. Suitable buffers or carriers include PBS or similar solutions at a physiologically neutral pH. Direct injection could be accomplished by a specially designed catheter designed delivery system.

For cardiac administration of the polynucleotide preparation, Adult Sprague-Dawley rats are anesthetized with 100 mg/kg ketamine intraperitoneally and an upper midline abdominal incision is made. During the procedure the rats are ventilated through a 21 G catheter placed intratracheally. After subjecting the aortic vessel to trauma, 100–200 micrograms DNA in 50 microliters normal saline is injected at the site of the trauma using a syringe and needle.

While 100–200 microgram DNA is used in the examples disclosed herein, these quantities should not be construed as limiting to the scope of the invention. Administration of larger quantities of DNA to humans may be required in order to observe a similar effect. Optimization of the mode of administration and the doses used will require greater or lesser amounts of oligonucleotide sequence depending on the given condition. Further, the species of oligonucleotide and the modifications on the oligonucleotide are expected to influence the efficiency of uptake and it effect. Thus, those of ordinary skill in the art will make adjustments to the quantity of oligonucleotide delivered to the vasculature. The determination of optimum dosage amounts and preparation of standard dose/response curves are well known routine exercises in the pharmaceutical arts.

Controlled Release

Another method of contacting a cell with exogenous nucleotide sequences is through a controlled release composition. For example, antisense molecules combined with compositions such as polylactic acid polymers can be inserted in vivo in the form of an implant or stent, as will be well known to those of ordinary skill in the art. The antisense molecules in the implant or stent are expected to be continually released throughout an extended period of time.

Viral Vectors

Another method of introducing nucleotide sequences into SMCs, in one preferred embodiment, is to use viral vectors. Either plasmid DNA containing antisense sequences, or RNA (Retrovirus) could be used. The methods necessary to insert plasmid DNA or RNA into viral vectors is well known to those skilled in the art. A coronary catheter could be used to place the viral particles in close proximity to the target SMCs.

CONCLUSION

Those of ordinary skill in the art will recognize that the present invention can be practiced in a variety of manners not specifically disclosed herein. These variations are to be included as within the scope of the present invention, when the invention is considered in light of the appended claims.

We claim:

1. A method of inhibiting the growth of a human smooth muscle cell, comprising contacting said cell with a synthetic antisense oligonucleotide directed against a c-myc gene product in an amount effective to inhibit translation of said c-myc gene product in said cell.

2. The method of claim 1 wherein said c-myc gene product has an AUG translation initiation codon, and said synthetic antisense oligonucleotide is complementary to a portion of a 27 nucleotide sequence of said c-myc gene product extending from two codons upstream of the AUG translation initiation codon to six codons downstream of the AUG translation initiation codon.

3. The method of claim 2 wherein said synthetic antisense oligonucleotide is complementary to a region of said c-myc gene product that extends from said AUG translation initiation codon to four codons downstream of said AUG translation initiation codon.

4. The method of claim 3 wherein said synthetic antisense oligonucleotide is chemically modified with phosphoramidate linkages to block exonucleolytic degradation.

5. The method of claim 2 wherein said synthetic antisense oligonucleotide is complementary to a region of said c-myc gene product that extends from one codon upstream of said AUG translation initiation codon to four codons downstream of said AUG translation initiation codon.

6. The method of claim 5 wherein said synthetic antisense oligonucleotide is chemically modified with phosphoramidate linkages to block exonucleolytic degradation.

7. A method of inhibiting the migration of a human smooth muscle cell, comprising contacting said cell with a synthetic antisense oligonucleotide directed against a c-myc gene product in an amount effective to inhibit translation of said c-myc gene product in said cell.

8. The method of claim 7 wherein said c-myc gene product has an AUG translation initiation codon, and said synthetic antisense oligonucleotide is complementary to a portion of a 27 nucleotide sequence of said c-myc gene product extending from two codons upstream of the AUG translation initiation codon to six codons downstream of the AUG translation initiation codon.

9. The method of claim 8 wherein said synthetic antisense oligonucleotide is complementary to a region of said c-myc gene product that extends from said AUG translation initiation codon to four codons downstream of said AUG translation initiation codon.

10. The method of claim 9 wherein said synthetic antisense oligonucleotide is chemically modified with phosphoramidate linkages to block exonucleolytic degradation.

11. The method of claim 9 wherein said synthetic antisense oligonucleotide is complementary to a region of said c-myc gene product that extends from one codon upstream of said AUG translation initiation codon to four codons downstream of said AUG translation initiation codon.

12. The method of claim 11 herein said synthetic antisense oligonucleotide is chemically modified with phosphoramidate linkages to block exonucleolytic degradation.

13. A method of inhibiting restenosis of a blood vessel in a human after mechanical treatment of the vessel to reduce a stenosis, the method comprising contacting the vessel with a synthetic antisense oligonucleotide directed against a c-myc gene product in an amount effective to inhibit translation of said c-myc gene product in the cells of the vessel.

14. The method of claim 13 wherein said c-myc gene product has an AUG translation initiation codon, and said synthetic antisense oligonucleotide is complementary to a portion of a 27 nucleotide sequence of said c-myc gene product extending from two codons upstream of the AUG translation initiation codon to six codons downstream of the AUG translation initiation codon.

15. The method of claim 14 wherein said synthetic antisense oligonucleotide is complementary to a region of said c-myc gene product that extends from said AUG translation initiation codon to four codons downstream of said AUG translation initiation codon.

16. The method of claim 15 wherein said synthetic antisense oligonucleotide is chemically modified with phosphoramidate linkages to block exonucleolytic degradation.

17. The method of claim 16 wherein said mechanical treatment is cardiac angioplasty.

18. The method of claim 16 wherein said synthetic antisense oligonucleotide is complementary to a region of said c-myc gene product that extends from one codon upstream of said AUG translation initiation codon to four codons downstream of said AUG translation initiation codon.

19. The method of claim 18 wherein said synthetic antisense oligonucleotide is chemically modified with phosphorapidate linkages to block exonucleolytic degradation.

* * * * *